(12) United States Patent
Salamon et al.

(10) Patent No.: US 11,660,250 B2
(45) Date of Patent: May 30, 2023

(54) METHOD AND APPARATUS FOR THERAPEUTIC GAS TREATMENT

(71) Applicant: Respiderm Corporation, Little Rock, AR (US)

(72) Inventors: Tibor Salamon, Little Rock, AR (US); Nagy Rihárd, Little Rock, AR (US); Hosszú Gergely, Little Rock, AR (US); Lászka Norbert, Little Rock, AR (US); Szakadati Zoltán, Little Rock, AR (US); Richard Rivers, Baltimore, MD (US)

(73) Assignee: Respiderm Corporation, Little Rock, AR (US)

( * ) Notice: Subject to any disclaimer, the term of this patent is extended or adjusted under 35 U.S.C. 154(b) by 205 days.

(21) Appl. No.: 16/772,333

(22) PCT Filed: Dec. 14, 2018

(86) PCT No.: PCT/US2018/065742
§ 371 (c)(1),
(2) Date: Jun. 12, 2020

(87) PCT Pub. No.: WO2019/118871
PCT Pub. Date: Jun. 20, 2019

(65) Prior Publication Data
US 2021/0077347 A1 Mar. 18, 2021

Related U.S. Application Data

(60) Provisional application No. 62/598,901, filed on Dec. 14, 2017.

(51) Int. Cl.
*A61H 33/14* (2006.01)
*A61H 33/06* (2006.01)
(Continued)

(52) U.S. Cl.
CPC ............ *A61H 33/14* (2013.01); *A61H 33/06* (2013.01); *A61H 35/00* (2013.01);
(Continued)

(58) Field of Classification Search
CPC ..................................................... A61H 33/14
(Continued)

(56) References Cited

U.S. PATENT DOCUMENTS 9,713,570 B2 * 7/2017 Török .................... A61H 35/00
2004/0129270 A1 7/2004 Fishman
(Continued)

FOREIGN PATENT DOCUMENTS

EP 2724702 A1 4/2014
JP 2003-235926 A 8/2003
(Continued)

OTHER PUBLICATIONS

International Search Report and Written Opinion for No. PCT/US2018/065742, dated Apr. 15, 2019.
(Continued)

*Primary Examiner* — Lori L Baker
(74) *Attorney, Agent, or Firm* — Merchant & Gould P.C.

(57) ABSTRACT

A handheld therapeutic apparatus and method of treatment are disclosed. In one example, the apparatus includes a valve system, a detachable gas cartridge housing unit that houses a gas cartridge or gas delivery from an outside gas cylinder in fluid communication with said valve system, a detachable treatment receptacle for the delivery of gas therapies is in fluid communication with said valve system, and a detachable nozzle in fluid communication with said valve system.

18 Claims, 53 Drawing Sheets

(51) Int. Cl.
*A61H 35/00* (2006.01)
*A61M 13/00* (2006.01)

(52) U.S. Cl.
CPC ............... *A61H 2033/145* (2013.01); *A61H 2201/5058* (2013.01); *A61M 13/003* (2013.01); *A61M 2202/0225* (2013.01); *A61M 2210/1433* (2013.01)

(58) Field of Classification Search
USPC .............. 604/24, 23, 56, 82, 26, 27, 28
See application file for complete search history.

(56) References Cited

U.S. PATENT DOCUMENTS

| | | |
|---|---|---|
| 2008/0167621 A1 | 7/2008 | Wagner et al. |
| 2015/0094576 A1 | 4/2015 | Levy et al. |

FOREIGN PATENT DOCUMENTS

| | | |
|---|---|---|
| JP | 2013-165976 A | 8/2013 |
| WO | 01/36018 A2 | 5/2001 |

OTHER PUBLICATIONS

European Search Report for corresponding EP Application 18888225.2 dated Apr. 12, 2022. (4 pages).

\* cited by examiner

METHOD AND APPARATUS FOR THERAPEUTIC GAS TREATMENT

This application is a National Stage Application of PCT/US2018/0065742, filed on Dec. 14, 2018, which claims the benefit of priority to U.S. Provisional Application Ser. No. 62/598,901, filed on Dec. 14, 2017, which applications are incorporated herein by reference. To the extent appropriate, a claim of priority is made to each of the above disclosed applications.

BACKGROUND

It is known that gases are important biological messenger molecules, and well-known gases and new gas pre-mixes show promising biological effects. Since ancient times, physicians have observed the positive effects of "carbon dioxide springs" for bathing and drinking. Balneotherapy—treatment through bathing—has been practiced for more than 120 years, for the treatment of cardiovascular (high blood pressure), diabetes mellitus, arthritis and osteoporosis conditions without side effects. Balneotherapies using naturally occurring carbonated water or springs containing carbon dioxide ($CO_2$) are some of the most thoroughly studied. All living animal and human bodies produce $CO_2$ as a by-product of cellular metabolism. Highly metabolic, aerobically active tissues produce high amounts of $CO_2$. There is a direct correlation between the amount of aerobic activity and the production of $CO_2$. Continuous metabolic activity also requires continuous delivery of oxygen ($O_2$) from the blood. The amount of blood flow to the tissue is precisely regulated according to the metabolic demand. A persistently high ratio of $CO_2$ to $O_2$ is an indication that the blood being supplied is not balanced with the tissue needs. If the biological signals that identify the need for blood persist for a prolonged period, a cascade is triggered for the formation of new blood vessels and the surrounding tissue to support it, thus increasing blood circulation, and lowering blood pressure.

In addition to the above positive effects, naturally occurring gases have low toxicity profiles. More and more studies also show the bacteriostatic effects of $CO_2$. Additionally, many scientists and researchers have increasingly been tackling the problem of delivering gaseous pharmacopeia drugs and other medical and purified gases, through the skin and directly to body cavities. Such delivery needs to occur without the side effects associated, for example, in specific transdermal applications with breaking the skin's natural barrier function, or dosage, pressure, and over inflation issues in case of cavity treatments, In recent years, $CO_2$ balneotherapies have become solidly grounded in the natural sciences. For example, in the European Union, Japan, Brazil, and other countries, health insurance companies have been reimbursing such treatments prescribed by physicians. Studies have evidenced that transdermal $CO_2$ diffusion increases when the skin is wet. This is why balneotherapies in carbonated water springs, where $CO_2$ is saturated in water, are effective. However, mineral-rich springs have begun to run dry places around the world. Further independent studies, have shown that high concentrations of $CO_2$ gas are needed for effective therapeutic treatments. It has also been determined that the desired long-term effects can only be obtained through serial applications.

A key challenge for the effective therapeutic use of artificial carbonated waters has been keeping the $CO_2$ in the water during the treatment periods. By virtue of its dipole moments, in contrast to $O_2$, it can bind and be stabilized by water molecules. Although $CO_2$ is 30 times more soluble than $O_2$ it also easily emitted from water. These characteristics are evident upon opening carbonated drinks, such as beers or sodas. Preventing the $CO_2$ from escaping by properly adjusting the concentration rate and evenly dispersing the $CO_2$ has posed technological barriers. If one can artificially achieve higher concentrations (1,000 parts per million) of $CO_2$, one can expect to benefit from similar effects on physiological functions as the above-described $CO_2$ balneotherapy.

Still further, delivery of $CO_2$ as a medical gas has many other applications. However, medical $CO_2$ systems tend to be bulky, awkward to operate, and costly. Thus, there exists a need for an effective, simple and convenient means for artificially producing carbonated springs and carbonic waters, as well as mixtures involving various other medicinal and therapeutic gases, that is also cost effective to manufacture. As mentioned above, $CO_2$ balneotherapy has been used to treat major conditions that affect hundreds of millions of people around the globe, such as osteoporosis, arthritis, diabetes mellitus and a variety of cardiovascular conditions. Additionally, $CO_2$ can have many other natural remedy effects, including, but not limited to, improving immunological responses and neurological functions, reducing swelling, enhancing the building of micro capillaries, increasing microvascular circulation and skin perfusion pressure, muscular strength, eliminating migraine headaches, etc.

Therefore, what is needed is a convenient, low cost means of administering a treatment to achieve the many positive effects of $CO_2$, as well as for administering other pharmaceutical medical or purified gases, for potential use in a wide range of applications in a wide variety of fields.

SUMMARY

In accordance with the following disclosure, the above and other issues are addressed by a handheld treatment apparatus for use in treating human and animal bodies with medical or therapeutic gases. These handheld treatment apparatuses may be used in administering a variety of therapeutic gases for numerous medical conditions, including but not limited to the treatment of tumors, wounds, and other cardiovascular and dermatological conditions. The apparatus may also be used to reduce recovery time after surgical procedures where tissue needs repair and incisions need enhanced healing. The apparatus may also be used for the intra-cavity delivery of $CO_2$, including but not limited to intra-cavity delivery to the uterus, bladder, rectum, stomach, sinuses, and pharynx. The apparatus may also be used to create bacteriostatic environment by providing a high $CO_2$ concentration environment for various procedures.

The handheld treatment apparatus may be separated into four distinct portions, the handle portion of the apparatus, the valve housing portion of the apparatus, the treatment receptacle portion of the apparatus and the nozzle portion of the apparatus with each distinct portion containing subcomponents. These four distinct portions of the overall handheld treatment apparatus are connected to one another to disperse therapeutic gases to patients.

The handle portion of the apparatus is adapted to receive a cartridge assembly containing a medical gas or mixture of medical gases. The cartridge assembly comprises a gas cartridge, containing a—medical gas or gas mixtures, and optionally a seal adapted to receive the gas cartridge. The handle portion is adapted to receive a plurality of sizes of cartridge assemblies. The cartridge assemblies being held in place within the handle portion directly or with a cartridge clip placed inside the handle portion. The handle portion of the apparatus may also be adapted to receive medical gases that are not available in portable size cartridge assemblies. For example, the handle portion of the apparatus may be adapted to receive the output from a larger industrial gas cylinder, an ozone generator, or other medical gas containers and gas generators.

The valve housing portion of the apparatus is in fluid communication with the handle portion, the treatment receptacle portion, and the nozzle portion of the treatment apparatus. The valve housing portion comprises a valve system which allows for the flow of medical gases.

The valve housing portion of the apparatus further comprises a cartridge piercing housing which further comprises a piercing pin. The cartridge piercing pin is adapted to pierce the gas cartridge of the cartridge assembly. In other embodiments the cartridge piercing pin is adapted to pierce a seal located either on the gas cartridge or inside the piercing housing when the handle portion is connected to the valve housing portion.

The valve housing portion of the apparatus may further comprise of an actuator button capable of starting and stopping the flow of gas through the valve system. The actuator button may be further adapted to control the quantity and speed of the medical gas as it flows through the valve system. In other embodiments the valve housing portion further comprises both an actuator button and a flow control dial. In such embodiments the actuator button controls the start and finish of gas flow while the flow control dial controls the maximum speed of gas flow through the valve system resulting in more refined control of gas speed and dosage released through the valve system. In still yet other embodiments the actuator button allows the user to control the emptying rate of the gas cartridge.

The valve system of the apparatus comprises a three-way valve in fluid communication with the gas cartridge assembly, the treatment receptacle portion, and the nozzle portion of the handheld apparatus. The valve system comprises of three flow lines which are adapted to allow medical gases to flow from the gas cartridge, through the treatment receptacle portion, and out the nozzle portion. The valve system of the apparatus may also further comprise several flow-control pins. The flow-control pins are adapted to only allow flow of the medical gas through the valve system when either, or both the treatment receptacle portion and, or the nozzle portion of the apparatus are properly engaged.

The treatment receptacle portion of the apparatus is adapted such that it is secured to the valve housing portion of the apparatus. When secured the valve housing portion of the apparatus, the treatment receptacle is in fluid communication with the valve system and the nozzle portion such that the gas flows through the treatment receptacle prior to flowing through the nozzle portion of the apparatus. In some embodiments, the treatment receptacle portion comprises a vapor treatment. The vapor treatment comprises a liquid reservoir adapted such the medical gas flows first through the liquid reservoir before flowing through the nozzle portion. In other embodiments, the treatment receptacle is a pressure gauge or meter. The pressure gauge is capable of measuring the flow rate, pressure, and other data of the gas flowing through the apparatus. The user is able to control the dosage of medical gas treatment by monitoring the readings from the pressure gauge.

The nozzle portion is adapted such that it is secured to the valve housing portion of the apparatus. The nozzle portion is in fluid communication with the valve system. In certain embodiments the nozzle portion may be rotated to control the level of gas or vapor expended from the treatment receptacle portion of the apparatus. In other embodiments the nozzle portion is adapted to receive attachments such as tubing, catheter, or attachments for performing ablation procedures.

The handheld treatment apparatus may be attached to a wearable receiver suit capable of receiving delivery of the gas to a desired treatment area or body part while the body part is in closed environment. In other embodiments the handheld treatment apparatus may be attached to a gas chamber cover capable of receiving delivery of medical gas to a space under which a patient is laying down with either the full body or partial body parts covered and isolated from outside environment. In other embodiments the handheld treatment apparatus may is adapted to deliver medical gases directly to an organ or intra-body cavity.

DETAILED DESCRIPTION

As briefly described above, a handheld treatment apparatus is described herein for use in delivering pharmacopeia, medical, and food grade gases and gas mixtures to a designated treatment area of a body. The apparatus may be divided into several distinct, detachable portions: a handle portion of the apparatus for housing a gas cartridge; a valve housing portion of the apparatus for housing a valve system; a treatment receptacle portion of the apparatus; and a nozzle portion of the apparatus. The valve system, housed within the valve housing portion is adapted such that it is in fluid communication with a gas cartridge assembly, the treatment receptacle portion and the nozzle portion of the apparatus. The nozzle portion may include detachable components including: a nozzle cap and a gas-vapor separator. The treatment receptacle may also include detachable components including: a liquid reservoir and a gas meter. When portions of the apparatus are fully assembled and properly engaged, medical gases are allowed to flow from the gas cartridge assembly contained in the handle portion through the valve system, to the treatment receptacle, and out the nozzle portion.

Figure 1:
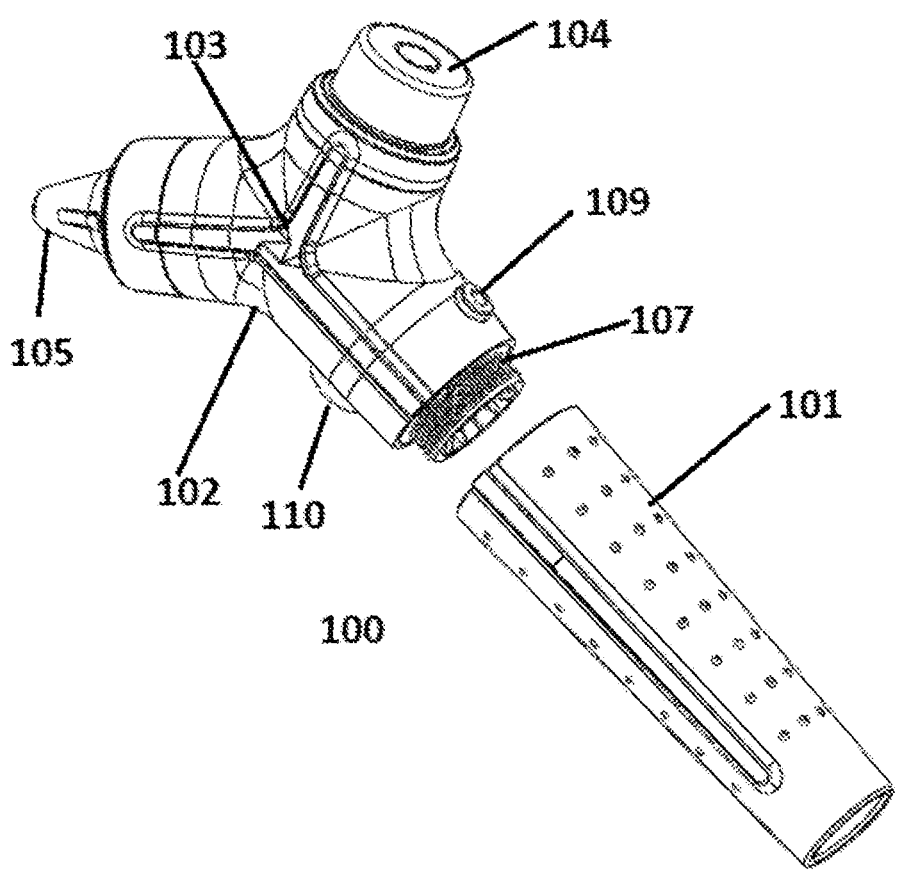
FIG. 1 illustrates a partially-exploded perspective view of the handheld treatment apparatus, with the handle portion of the apparatus detached from the valve housing portion.

As shown in FIG. 1, the apparatus 100 includes a separable handle portion 101, valve housing portion 102, and valve system 103. Apparatus 100 further comprises a treatment receptacle portion 104 and nozzle portion 105. In some embodiments apparatus 100 may also include an actuator button 109 for controlling the start and stop of the gas flow. In some embodiments apparatus 100 may also include a gas-flow-control dial 110 for controlling the flow of the gas. Apparatus 100 is generally sized and shaped for handheld operation, and can be operated by a user via either hand.

Figure 2:
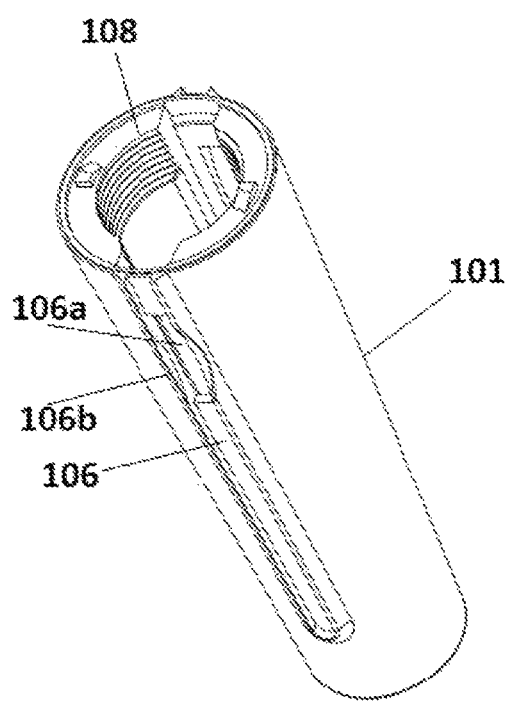
FIG. 2 illustrates a cross-sectional view of the handle portion.

Handle portion 101 may be constructed from any number of appropriate light-weight materials such as thermoset plastic polymers and resins. Handle portion 101 is adapted to receive neck 107 of valve housing portion 102 at collar 108 (shown in FIG. 2). In other embodiments neck 107 is adapted to receive handle portion 101. The handle portion 101 and valve housing portion 102 can be connected by variety of temporary fastening mechanisms. In some embodiments collar 108 is fastened to neck portion 107 through a force-fit connection. In other embodiments, collar 108 and neck 107 are fastened through a threaded connection.

Figure 3A:
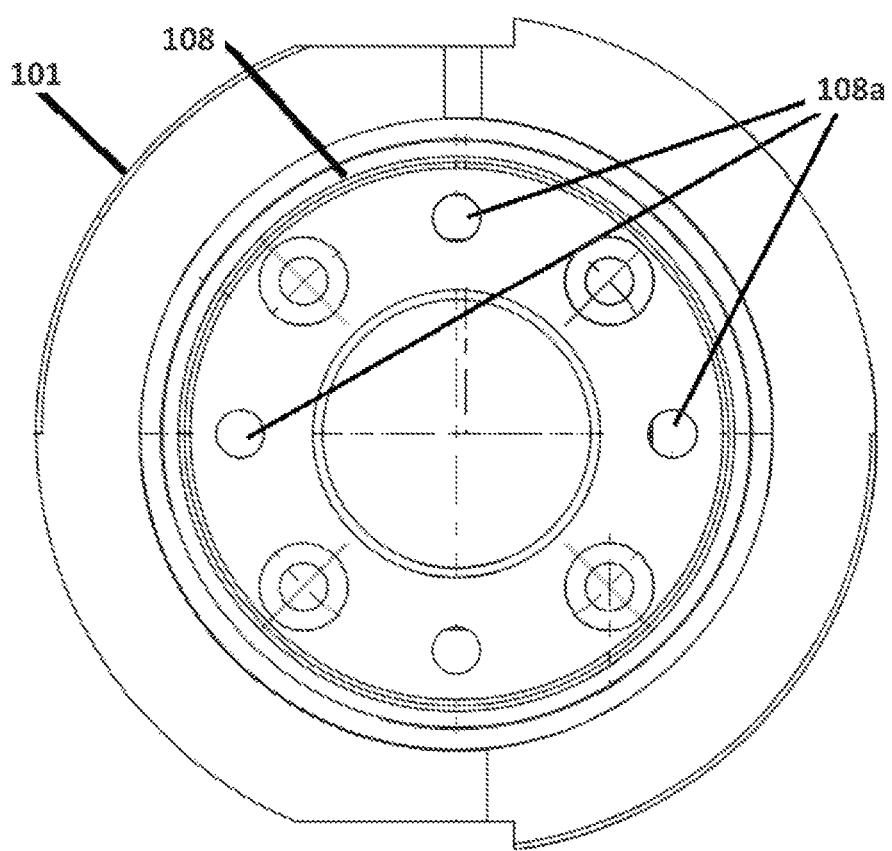
FIG. 3A illustrates a top view of the collar of the handle portion as well as the pressure release outlets.
Figure 3B:
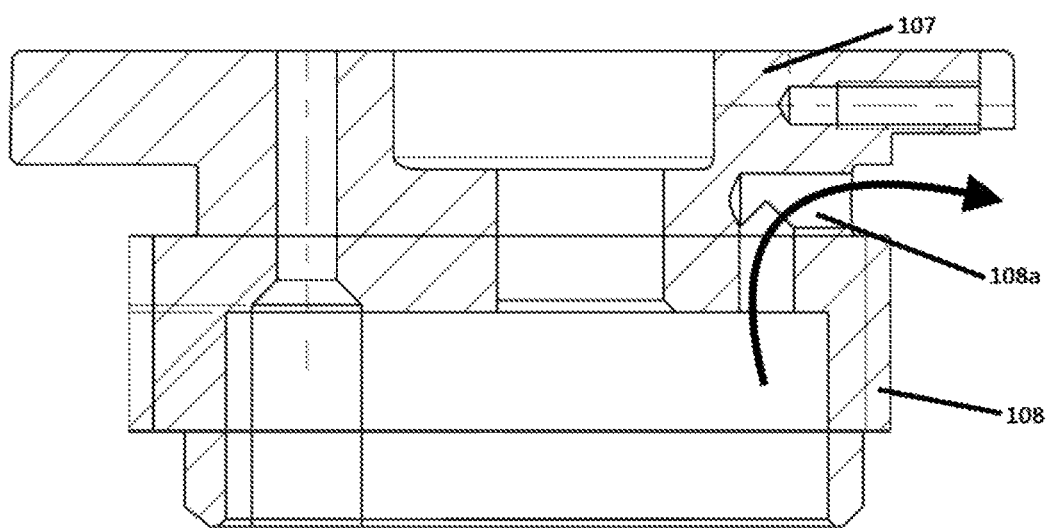
FIG. 3B illustrates a top and bottom view of the collar of the handle portion as well as the pressure release outlets.
Figure 4A:
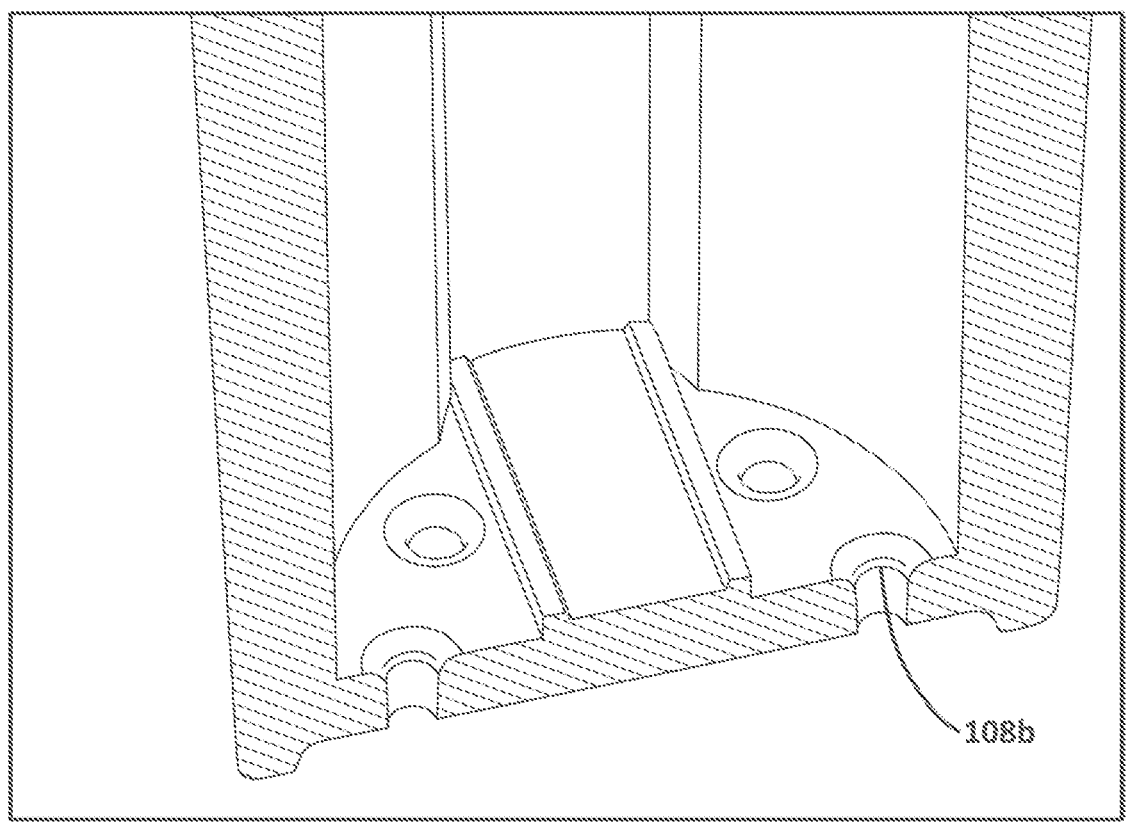
FIG. 4A illustrates the inside view of the handle portion with pressure release outlets.
Figure 4B:
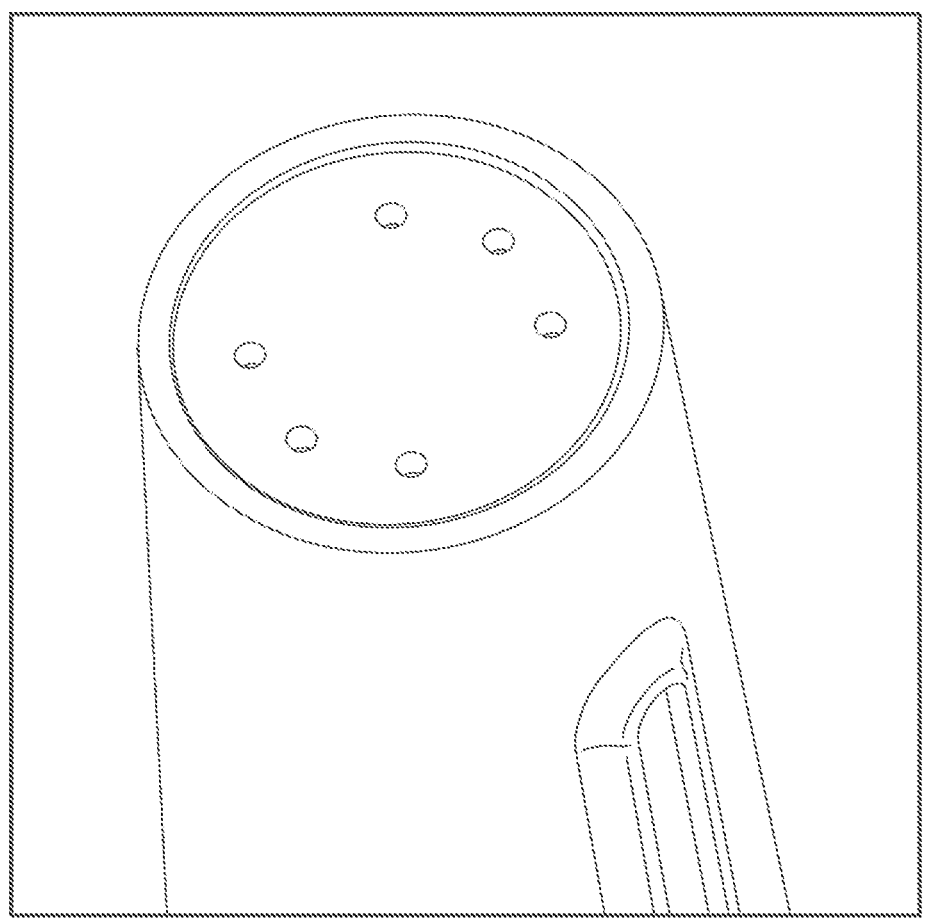
FIG. 4B illustrates the bottom view of the handle portion with pressure release outlets.
Figure 5:
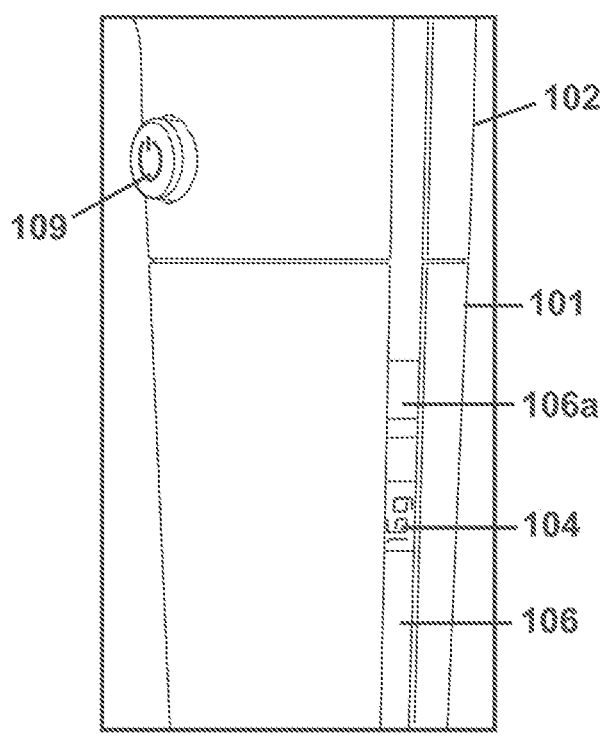
FIG. 5 is a side view of a handle portion of the apparatus with a 16g cartridge clip placed inside and the actuator button on the valve housing portion.

In some embodiment neck 107 is adapted to have gas outlets. In other embodiments collar 108 is adapted to have gas outlet holes 108a as shown in FIG. 3A. Gas outlet 108a prevent handle portion 101 from over pressurizing during operation. As seen in FIG. 3B, gas outlet holes 108a allow gas to flow between gas cartridge 300 and pin housing 401 of the neck portion 107 and outside space thus preventing gas to travel downward into handle portion 101 while handle portion 101 is being disassembled but still connected to neck 107. In some embodiments gas outlets 108a are L-shaped. In other embodiments gas outlets 108a are straight. In still yet other embodiments gas outlet 108a are curved. In some embodiments handle portion 101 is adapted to have additional gas outlets 108b. Gas outlets 108b may be present anywhere long the body of handle portion 101. In some embodiments gas outlets 108b are located on the bottom of the handle as illustrated in FIGS. 4A and 4B. FIG. 5 provides an illustration of handle portion 101 fastened to valve housing portion 102.

Figure 6:
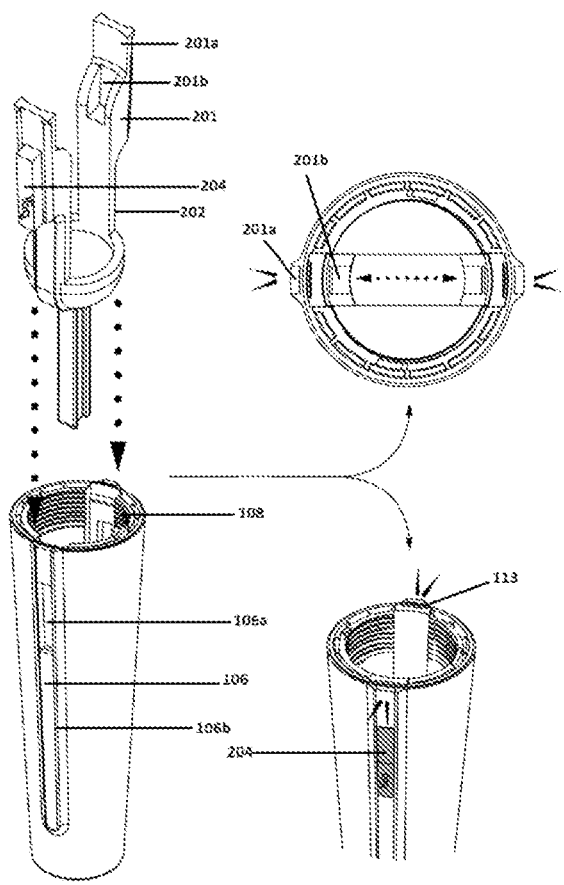
FIG. 6 illustrates a partially exploded perspective view of the handle portion of the apparatus as well as the side and bottom views of the cartridge clip.
Figure 7:
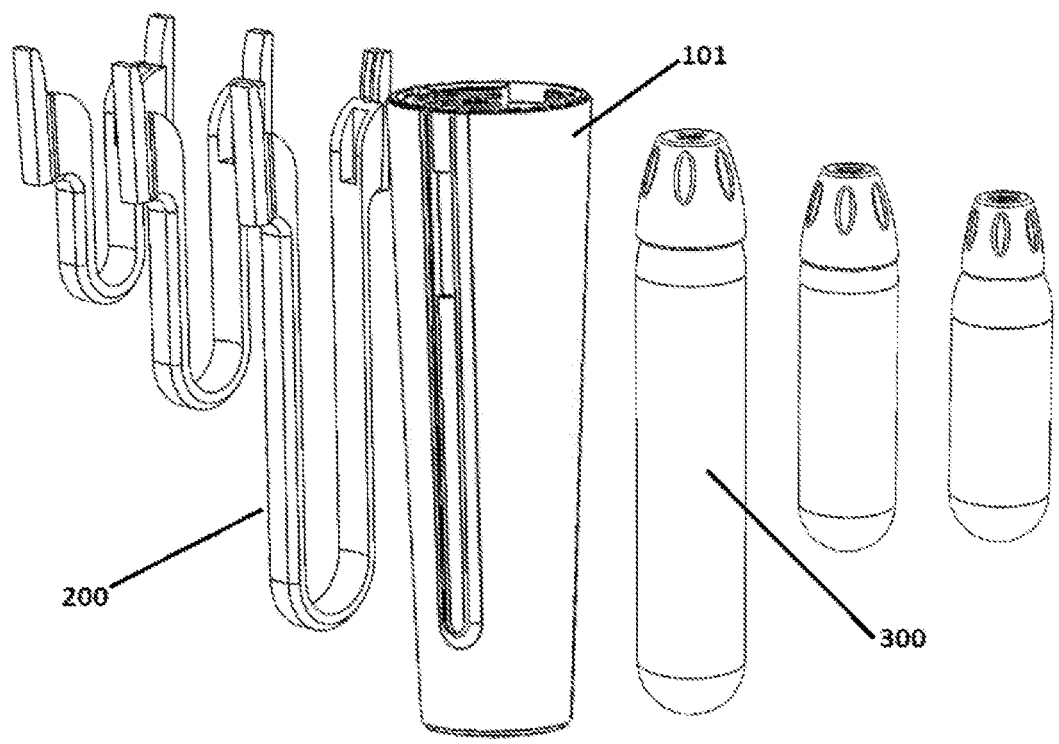
FIG. 7 is a side view of the handle portion of the apparatus as well as various sizes of cartridge assemblies and cartridge clips.
Figure 43:
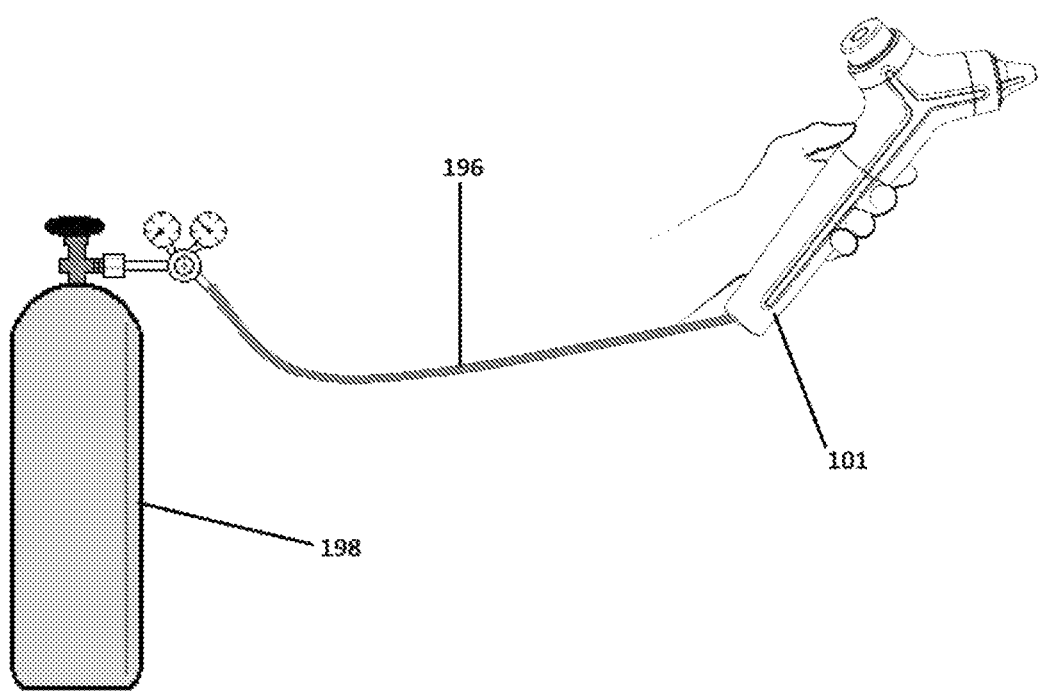
FIG. 43 illustrates the handle portion of the apparatus connected to an external gas cylinder.

Referring back to FIG. 2, handle portion 101 further comprises of channel 106. In some embodiments channel 106 further comprises transparent window 106a and recess 106b which runs parallel along each edge of channel 106. As shown in FIG. 6, the handle portion 101 of the apparatus can be adapted to receive a gas cartridge assembly 300. This feature is achieved by engagement of gas cartridge clip 200 with handle portion 101. As shown in FIG. 7, both the cartridge clip 200 and gas cartridge assembly 300 may come in a variety of sizes, all of which are adapted to fit into the handle portion 101 or can be connected to the handle portion 101. In some embodiments handle portion 101 may be made to accept and fit to specific cartridge assemblies 300 without gas cartridge clip 200. As illustrated in FIG. 43, in some embodiments handle portion 101 is adapted to receive tubing 196 allowing for an external gas cylinder 198 to be connected to the handle portion 101. Tubing 196 may be constructed from any suitable material including but not limited to polyethylene, polypropylene, polyvinylchloride, aluminum, and stainless steel. In other embodiments, the handle potion 101 is adapted to connect to the output of a larger industrial gas cylinder, an ozone generator, or other medical gas containers and gas generators.

Figure 8:
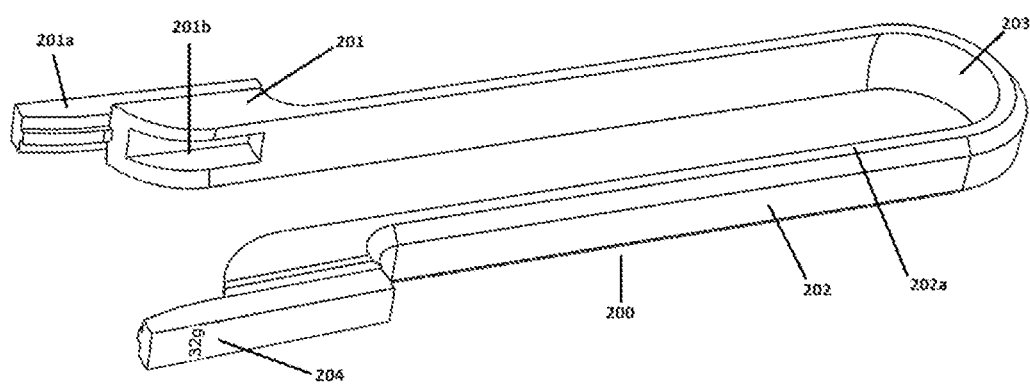
FIG. 8 is a side view of an example cartridge clip.
Figure 9:
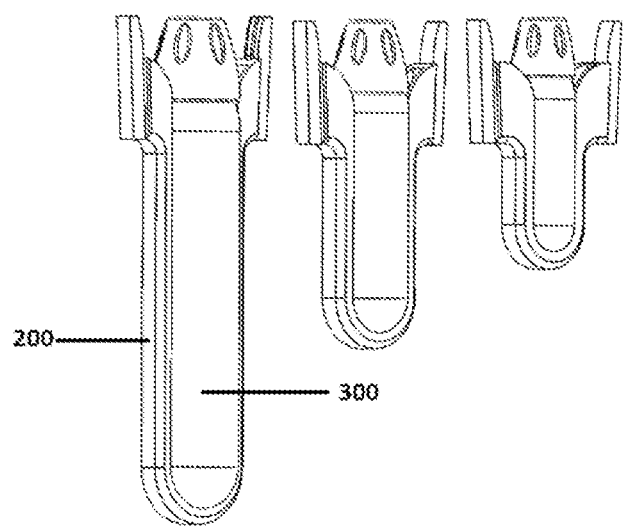
FIG. 9 illustrates a plurality of different cartridge assemblies held by correspondingly-sized cartridge clips.

FIG. 8 shows a side-view of an illustrative gas cartridge clip 200. Cartridge clip 200 is symmetrical and comprises a main body portion with two proximal end members 201, two arm members 202, and a distal end member 203. Proximal end member 201 is adapted to engage handle portion 101. Proximal end member 201 further comprises locking tab 201a and recess 201b. Recess 201b, located on the inward facing surface of proximal end member 201 is adapted to receive gas cartridge assembly 300 as shown in FIG. 9. In some embodiments recess 201b is curved. In other embodiments recess 201b is tapered.

Figure 10:
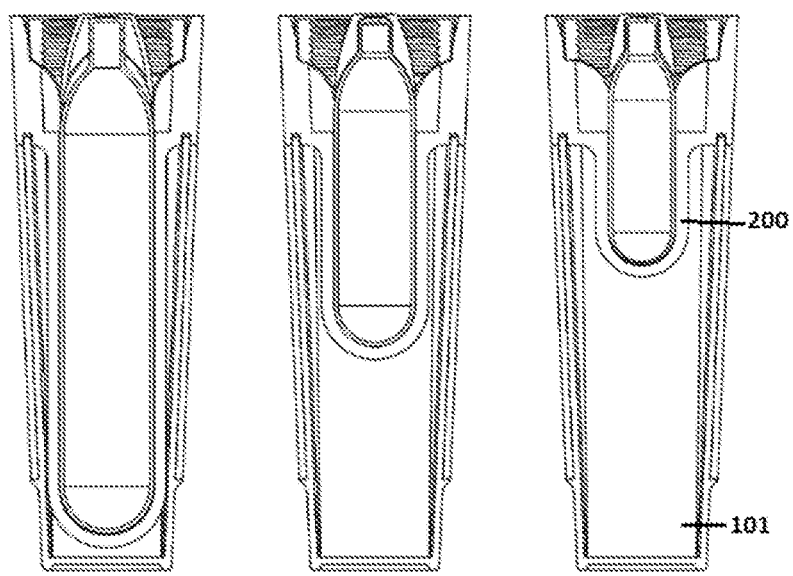
FIG. 10 illustrates a plurality of handle portions of the apparatus, including cartridge assemblies and cartridge clips having different sizes fitting into the handle portion of the apparatus.

Locking tab 201a is located on the outward facing surface of proximal end member 201. Referring back to FIG. 6, locking tab 201a is received by slot 113 of handle portion 101. When locking tab 201a is engaged in slot 113, cartridge clip 200 is prevented from moving vertically within handle portion 101. This allows the same handle portion 101 to accommodate various sizes of gas cartridges as shown in FIG. 10. In some embodiments locking tab 201a may further comprise label 204 for identifying the size and type of gas cartridge assembly 300 in the handle portion 101. Label 204 is visible through transparent window 106a, as shown in FIG. 6. In some embodiments label 204 includes written indicia identifying the capacity of the gas cartridge. In some embodiments international color codes for medical gases are visible through transparent window 106a allowing the user to identify the type of medical gas being used at any given time.

Arm members 202 are adapted to both support gas cartridge 300 and engage handle portion 101. Arm members 202 are adapted to fit within channel 106 of handle portion 101. The engagement of arm members 202 with channel 106 prevents rotational movement of cartridge clip 200. In some embodiments arm members 202 may be adapted to have edge surface 202a which slides within recess 106b located on the inside edge of channel 106 which provides an additional mechanism for preventing rotational movement of cartridge clip 200 during use of apparatus 100. In some embodiments recess 106b and edge surface 202a are curved. In other embodiments recess 106b and edge surface 202a are tapered. In still yet other embodiments recess 106b and edge surface 202a are planar.

Cartridge clip 200 may be inserted into handle portion 101 prior to insertion of the corresponding gas cartridge 300. The size of cartridge clip 200 is selected to ensure that gas cartridge assembly 300 is at the correct height. Cartridge clip 200 can be fashioned out of any rigid or semi-rigid material. Examples of appropriate materials include but are not limited to moldable plastics and metals such as aluminum. In some embodiments proximal end members 201, arm members 202, and distal end member 203 may be fabricated as individual components and assembled prior to use of apparatus 100. This feature allows the end user to adjust the size of gas cartridge clip 200 on demand, based on the size of the gas cartridge 301. In other embodiments cartridge clip 200 may be fabricated as a single piece, such as through an injection molding process or 3D printing. In these embodiments, the size of the cartridge clip 200 is predetermined based on reported standardized gas cartridge sizes or other specifications based on custom gas cartridge designs.

Figure 11:
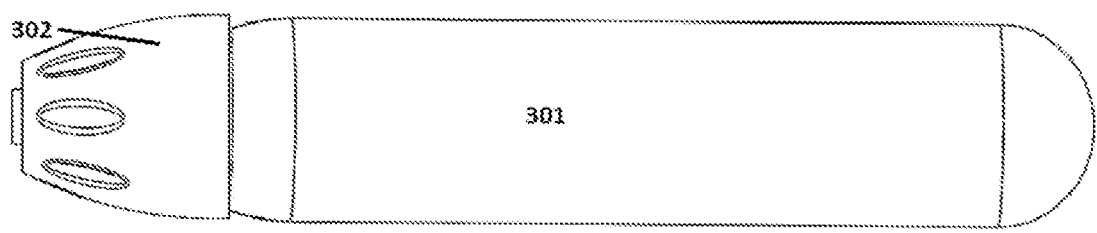
FIG. 11 shows an exterior view of a gas cartridge assembly with a seal.
Figure 12:
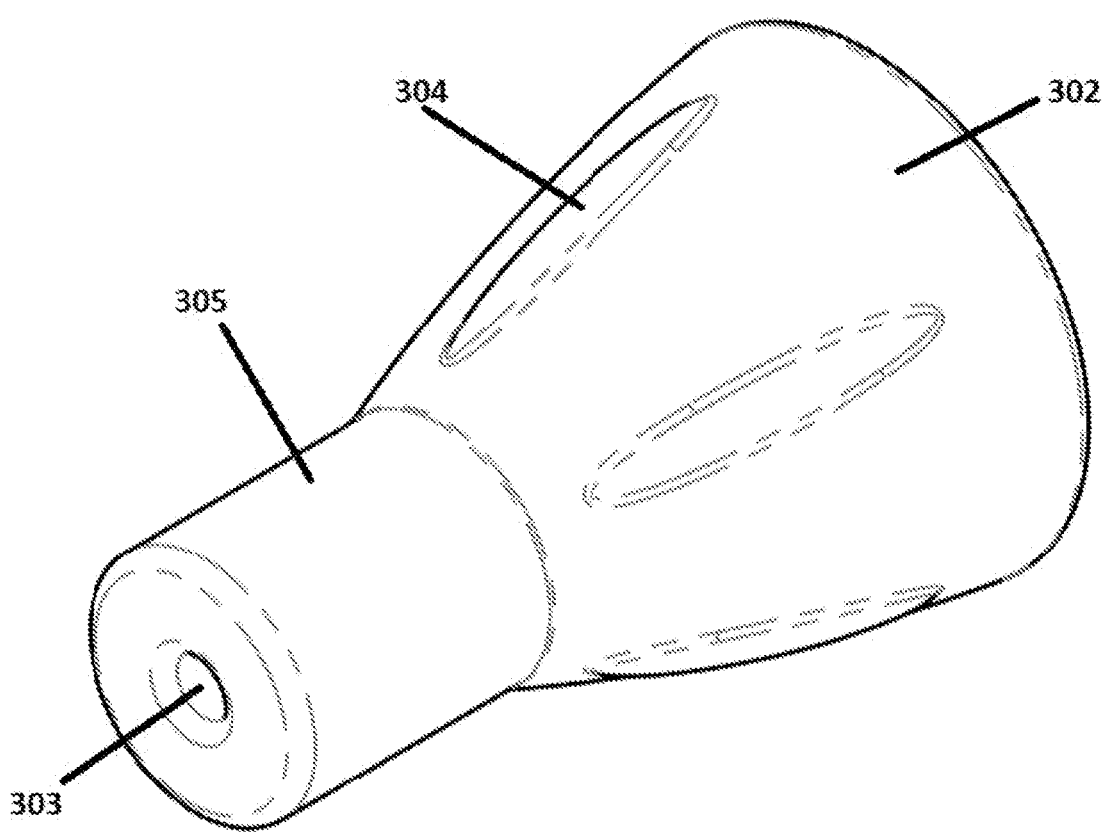
FIG. 12 shows the exterior of the seal that is attached to a gas cartridge.
Figure 13:
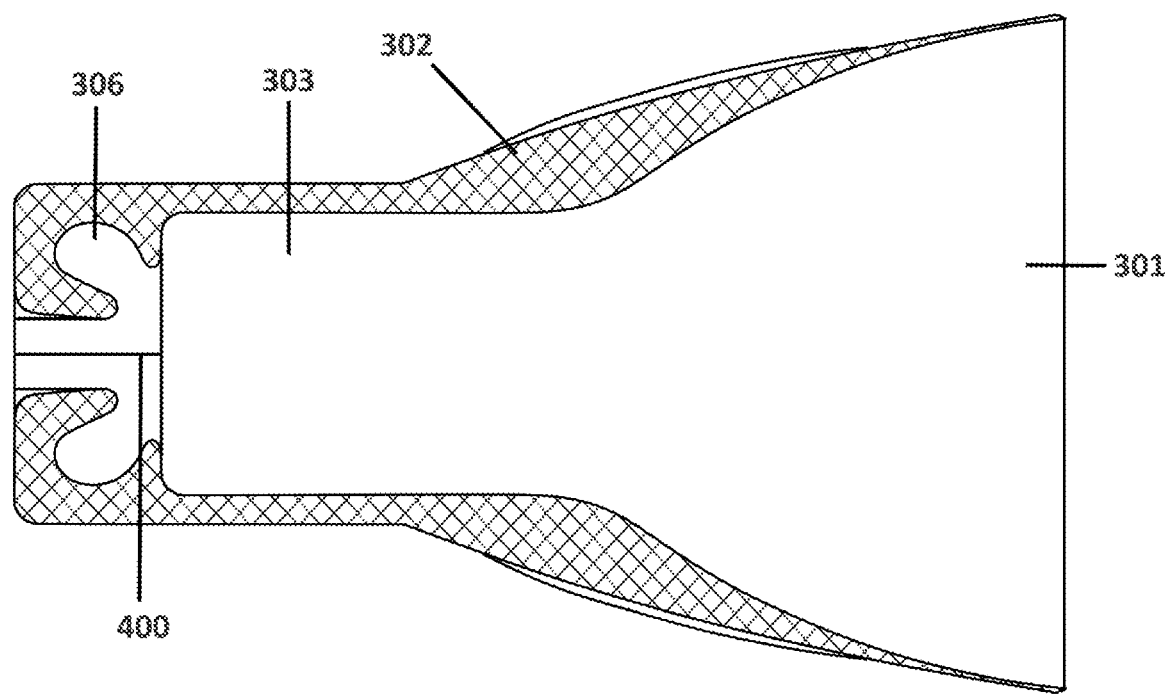
FIG. 13 shows the seal that as attached to a gas cartridge.
Figure 14:
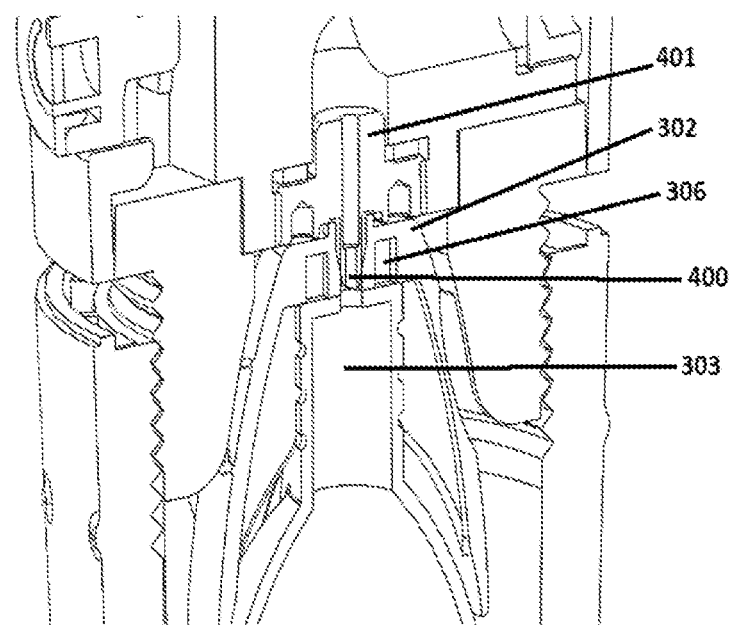
FIG. 14 illustrates an interior partial cross-sectional view of the handle portion engaged with the valve housing portion.

As referenced above, gas cartridge assembly 300 can come in a variety of sizes as shown in FIG. 7. Gas cartridges 301 are also available for a variety of medical gases. As illustrated in FIG. 11, gas cartridge assembly 300 may comprise of seal 302 and a gas cartridge 301. Seal 302 is affixed to gas cartridge 301 at neck 305. FIG. 12 illustrates the external structure of seal 302. Seal 302 is perforated 304 so that any attempt to remove seal 302 will cause tearing in the intercostal spaces, rendering gas cartridge assembly 300 unusable. Gas injection port 303 is located in the center of seal 302. In some embodiments injection port 303 is threaded which allows for seal 302 to be fastened to a similarly threaded or non-threaded gas cartridge 301. In other embodiments seal 302 is affixed with an adhesive. As illustrated in FIG. 13, seal 302 is affixed to gas cartridge 301 such that cavity 306 is present between gas cartridge neck 303 and seal 302. Cavity 306 allows for an airtight seal between gas cartridge assembly 300 and pin housing 401. Cavity 306 is filled with gas after piercing pin 400 pierces cartridge 301 through injection port 303. Shown in FIG. 14, as cavity 306 fills with gas, the gas exerts outward pressure on the internal walls of seal 302 pressuring its outside walls to fill gaps between seal 302 and pin housing 401. Seal 302 with cavity 306 allows the gas cartridge 301 to be inserted into pin housing 401 deeper without any resistance. Seal 302 also minimizes temperature transfer between gas cartridge 301 and valve system 103, preventing incidental freezing of liquid due to cooling of gas cartridge 301 when in use.

In preferred embodiments seal 302 is construction from a silicon material. In some embodiments seal 302 is constructed from an epoxy-based resin. In other embodiments seal 302 is constructed from rubber based materials commonly used for high pressure gas cartridges. The internal structure seal 302 can be customized to any size, length or width with any type of thread or non-threaded gas cartridge.

Figure 15:
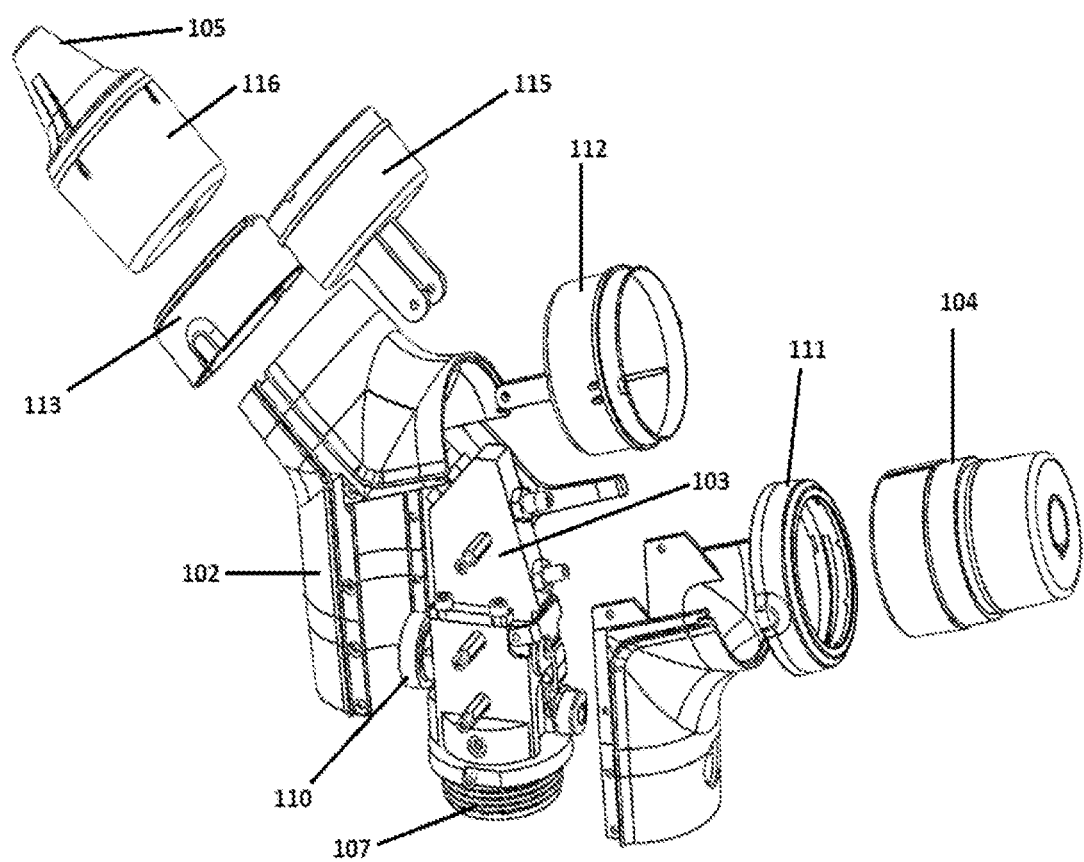
FIG. 15 is an exploded view of the valve housing portion of the apparatus with the treatment receptacle and nozzle portions.

FIG. 15 depicts an exploded view of the valve housing portion 102. Valve housing portion 102 connects to handle 101, treatment receptacle 104 and nozzle portion 105. Valve housing 102 also encloses valve system 103. In all embodiments the connection between treatment receptacle 104 and valve housing portion 102 is airtight. In all embodiments the connection between nozzle portion 105 and valve housing portion 102 is airtight. In some embodiments, receptacle treatment portion 104 and nozzle portion 105 are affixed to valve housing portion 103 by collars 111 and 113. In some embodiments collars 111 and 113 are threaded. In other embodiments collars 111 and 113 are attached through force-fit connections. In other embodiments, collars 111 and 113 are pressure fit or force fit around valve housing fasteners 112 and 115.

Valve housing fastener 112 resides within valve housing portion 102 and provides for easy connection of treatment receptacle 104 to valve housing 102. Likewise, valve housing fastener 115 resides within valve housing portion 102 and provides for easy connection of nozzle portion 105. In some embodiments receptacle treatment portion 104 is attached to valve housing portion 102 by first engaging valve housing fastener 112 and then being further secured by collar 111. Similarly, in some embodiments nozzle portion 105 is attached to valve housing portion 102 by first engaging gas-vapor separator 116 with valve housing fastener 115 and then being further secured by collar 113.

Figure 16:
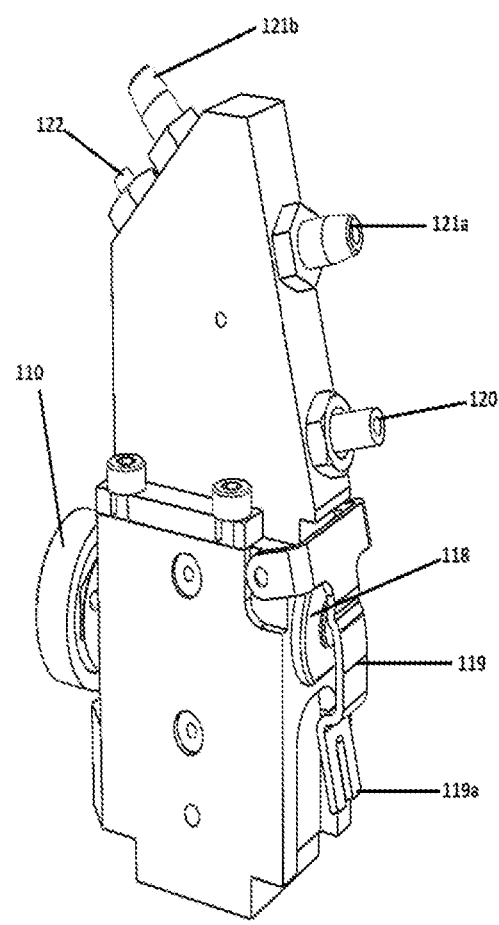
FIG. 16 is an exterior view of the valve system of the apparatus with the valve housing removed.

FIG. 16 depicts valve system 103. Valve system 103 is a three-way valve which controls the flow of medical gases from gas cartridge assembly 300 through treatment receptacle 104 and nozzle portion 105. As shown in FIG. 16, valve system 103 has a series of ports 120, 121a, 121b, and 122. Ports 120 and 121a are in fluid communication with treatment receptacle 104. Ports 121b and 122 are in fluid communication with nozzle portion 105. Valve system 103 may further comprise an actuator button 109 and gas flow-control dial 110. In some embodiments valve system 103 may have only an actuator button. In other embodiments valve system 103 may have only gas flow-control button.

Figure 17:
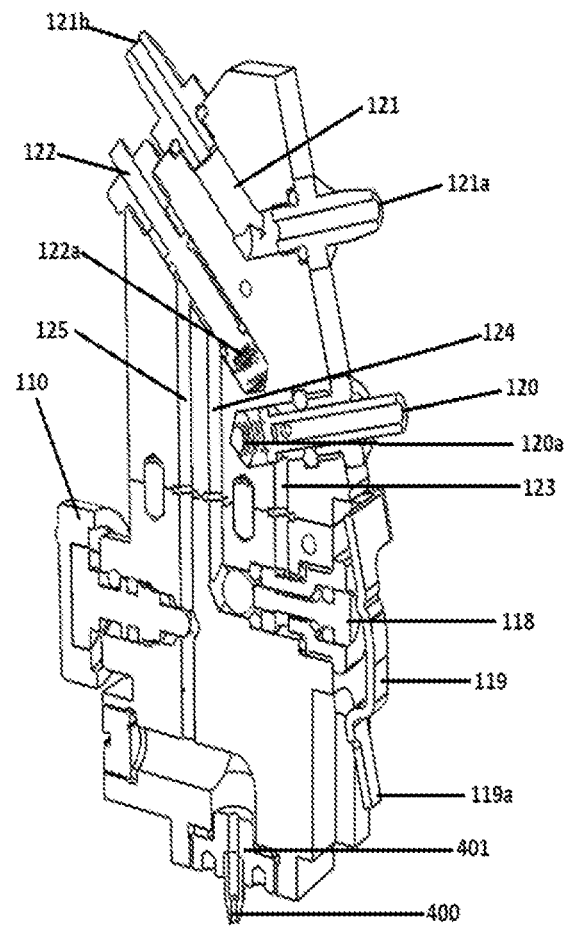
FIG. 17 is a cross sectional view of the valve system of the apparatus.
Figure 23:
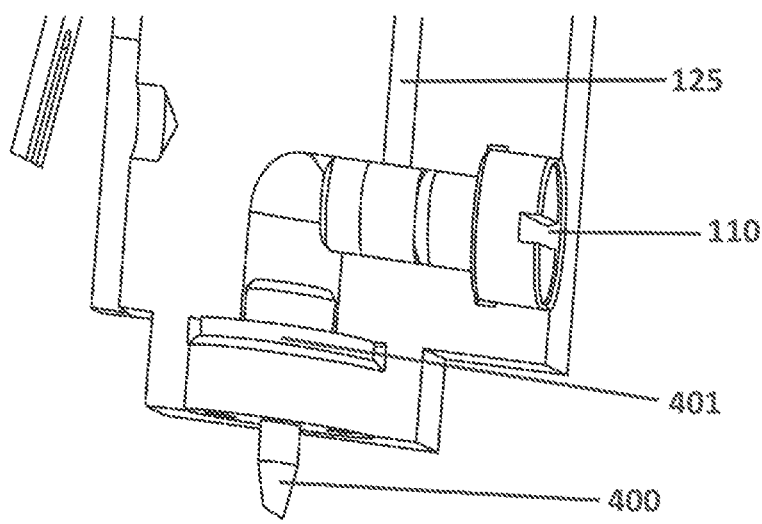
FIG. 23 is a cross sectional view of the flow-control dial in a flow limiting position.
Figure 24:
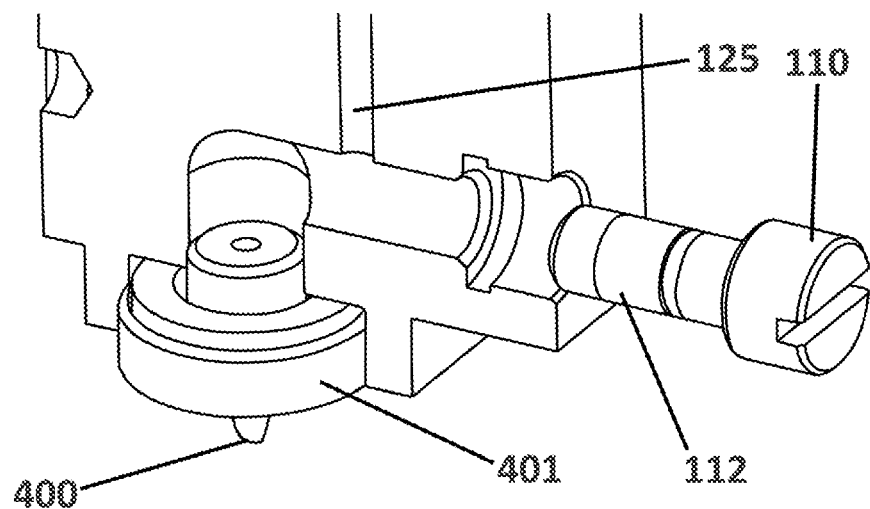
FIG. 24 is a cross sectional view of the flow-control dial in a flow allowing position.

The cross sectional view from FIG. 17 provides a more detailed explanation of the path of gas flow through valve system. Valve system 103 comprises three flow channels, 123, 124, and 125, which control the flow of gas from the gas cartridge assembly through the treatment receptacle and out the nozzle. In addition valve system 103 has flow channel 121 which provides for fluid communication between treatment receptacle 104 and nozzle portion 105. Flow channel 125 provides a flow path between gas cartridge assembly 300 and the rest of valve system 103. As described above, piercing pin 400 pierces gas cartridge assembly 300 creating an airtight seal between cartridge assembly 300 and pin housing 401. Upon piercing, medical gas flows out of cartridge assembly 300 and into valve system 103. Medical gas enters valve system 103 through flow channel 125. In some embodiments, the flow of gas through flow channel 125 is controlled by gas-flow speed dial 110. As depicted in FIGS. 23 and 24, gas-flow speed dial 110 is adapted to obstruct the flow of gas through flow channel 125 when dial 110 is in a closed position. When dial 110 is in an open position, as shown in FIG. 24, gas is allowed to flow through flow channel 125.

Figure 18:
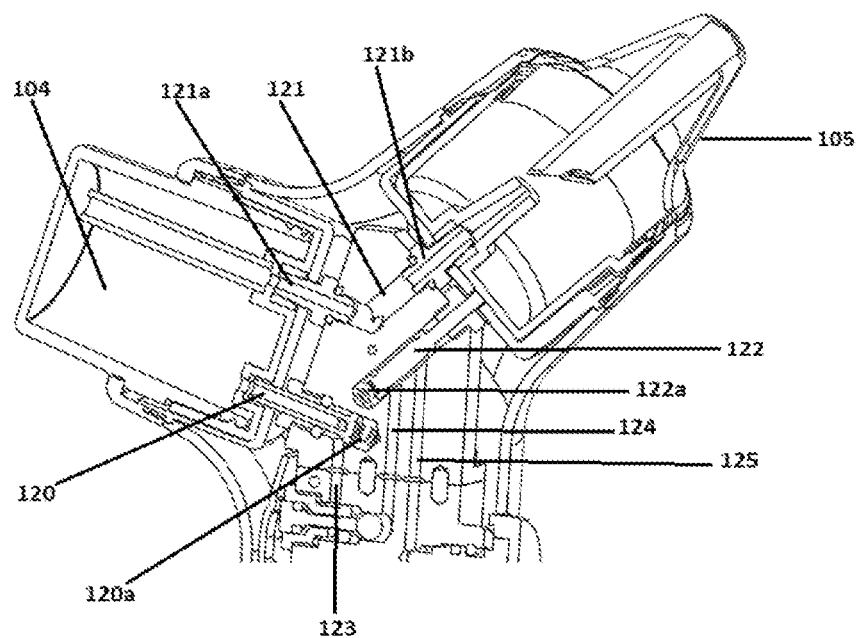
FIG. 18 is a cross sectional view of the valve system of the apparatus, with the treatment receptacle portion and the nozzle portion engaged.
Figure 19:
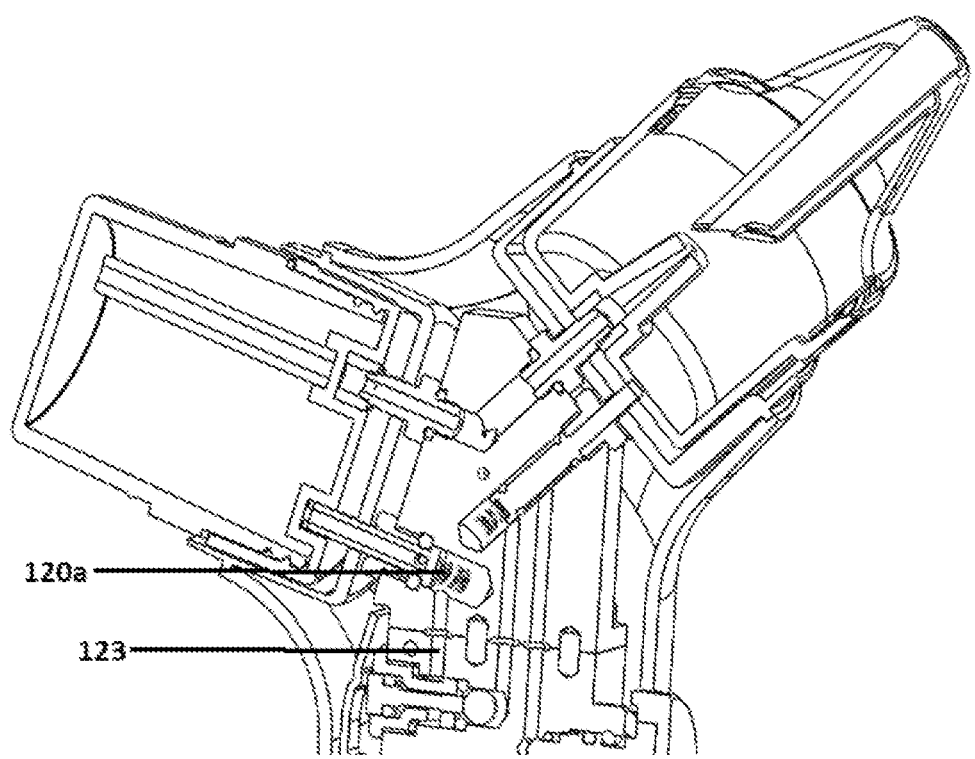
FIG. 19 is a cross sectional view of the valve system of the apparatus, with the treatment receptacle portion not engaged.

Referring back to FIG. 17, flow channel 125 extends from pin housing 401 to port 122. As described above port 122 is in fluid connection with nozzle portion 105. Port 122 also contains valve pin 122a. Valve pin 122a is adapted to control the flow of gas between flow channel 125 and flow channel 124. Valve pin 122a is biased outward and compressible inward. When nozzle portion 105 is properly engaged, such that an airtight seal is created between valve housing 102 and nozzle portion 105, valve pin 122a is compressed inward allowing gas to flow from flow channel 125 into flow channel 124 through port 122 as illustrated by FIG. 18. Contrastingly, when nozzle portion 105 is not properly engaged, e.g. an airtight seal is not formed between 102 and 105, valve pin 122a is not compressed and remains biased outward as shown in FIG. 19. When valve pin 122a is biased outward, gas flow to flow channel 124 is blocked. Thus preventing the flow of gas from flow channel 125 to flow channel 124 through port 122.

Figure 20:
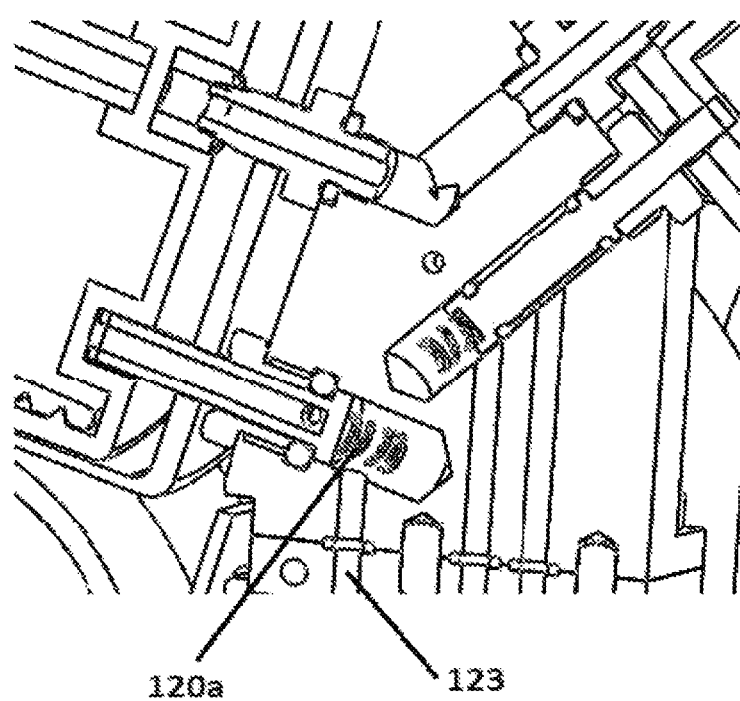
FIG. 20 is a close up cross sectional view of the valve pins disengaged.

Port 120 contains valve pin 120a which operates in a similar manner to valve pin 122a. Valve pin 120a is outward biased and compressible inward. When treatment receptacle 104 is properly engaged, such that an airtight seal is created between valve housing 102 and treatment receptacle 104, valve pin 120a is compressed inward allowing for the flow of gas from flow channel 123 into treatment receptacle 104 through port 120 as illustrated by FIG. 18. Contrastingly, when treatment receptacle portion 104 is not properly engaged, e.g. an airtight seal is not formed between 102 and 104, valve pin 120a is not compressed and remains biased outward as shown in FIG. 19. When valve pin 120a is biased outward, gas flow to receptacle treatment portion 104 is blocked. Thus preventing the flow of gas from flow channel 123 to treatment receptacle 104 through port 120. FIG. 20 provides a detailed view of valve pins 120a and 122a. Valve pins 120a and 122a are adapted such that they are biased outward and compressible inward. In some embodiments valve pins 120a and 123a are biased by a spring. In other embodiments valve pins 120a and 123a operate as ball and socket valves.

Figure 21:
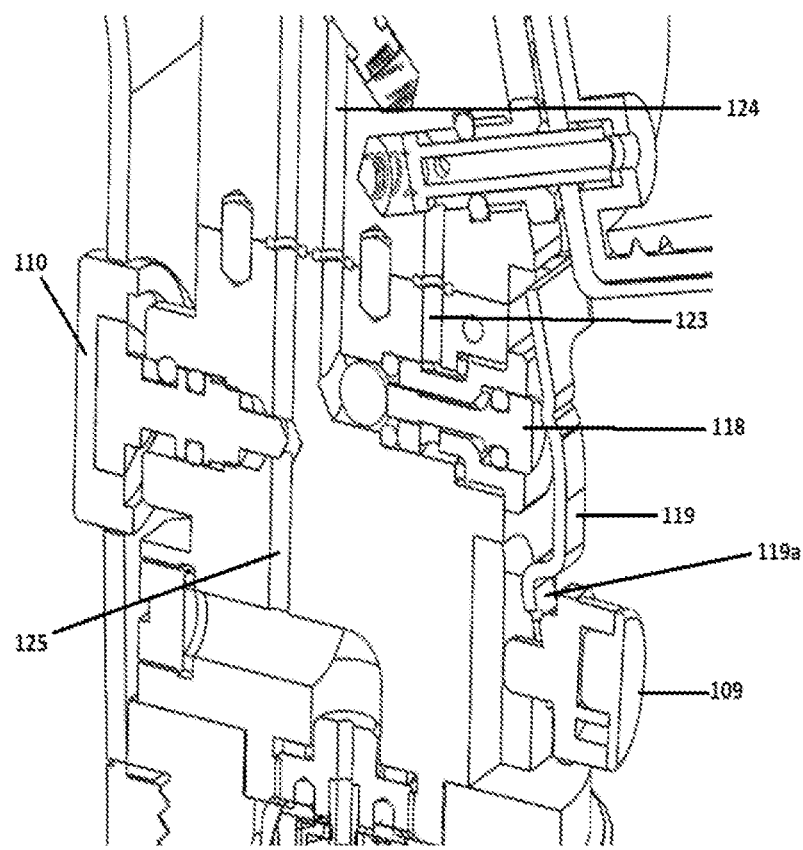
FIG. 21 is a close up cross sectional view of the valve system of the apparatus, the actuator button, and the gas-flow-control dial.
Figure 22:
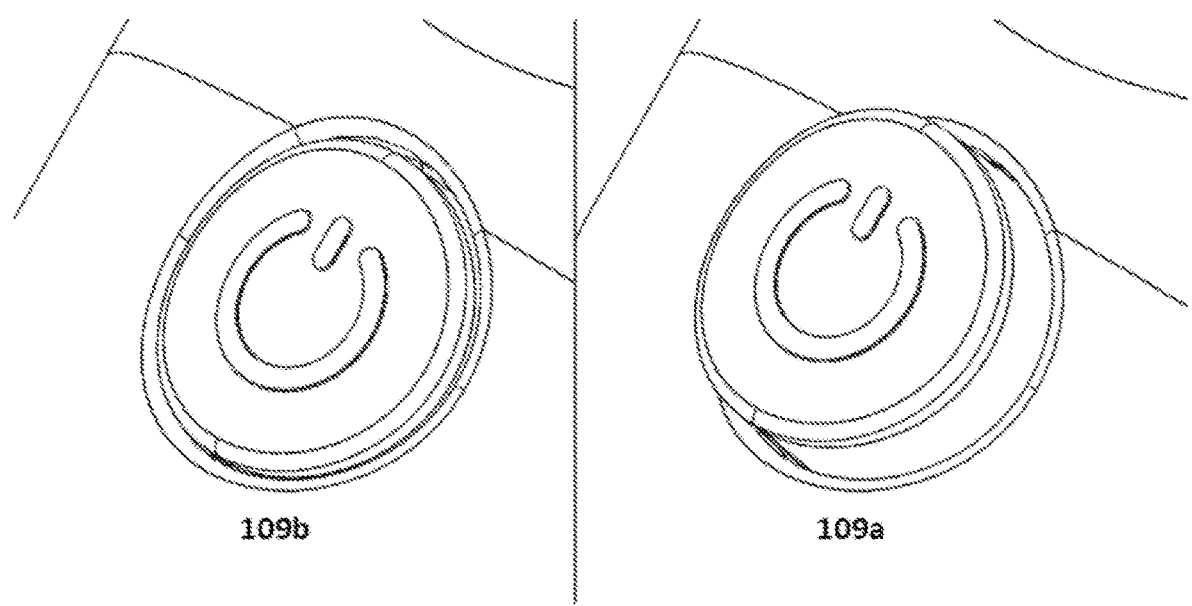
FIG. 22 illustrates the actuator button in first and second positions.

FIG. 21 illustrates the interaction of actuator button 109 with valve system 103. In general, when apparatus 100 is fully assembled, pressure from gas cartridge 301 will maintain the actuator button 109 in a protruded position 109a as shown in FIG. 22. When actuator button 109 is in a protruded position, forcing arm 119 is engaged with pin 118.

Depressing actuator button 109a (FIG. 22) causes forcing arm 109 to disengage pin 118. Forcing arm 119 confers a mechanical advantage to actuator button 109, allowing the user to stop the flow of gas through valve system 103, regardless of the overall pressure within the system.

Additionally, the quantity and the speed of gas allowed to pass through the system at any given time frame may be regulated by the gas-flow-control dial 110. FIGS. 23 and 24 show how incrementally depressing gas flow-control dial 110 pushes the controlling pin 112 into valve system 103, thus regulating the quantity and the speed of gas that is allowed to pass through valve system within a certain timeframe 103. The more gas speed control button 110 is depressed, the slower the gas is allowed to travel through valve system resulting smaller quantity of gas passing through during a given timeframe 103. The control of gas flow by flow-control dial 110 is an important for the intracavity delivery of medical gases.

Figure 25:
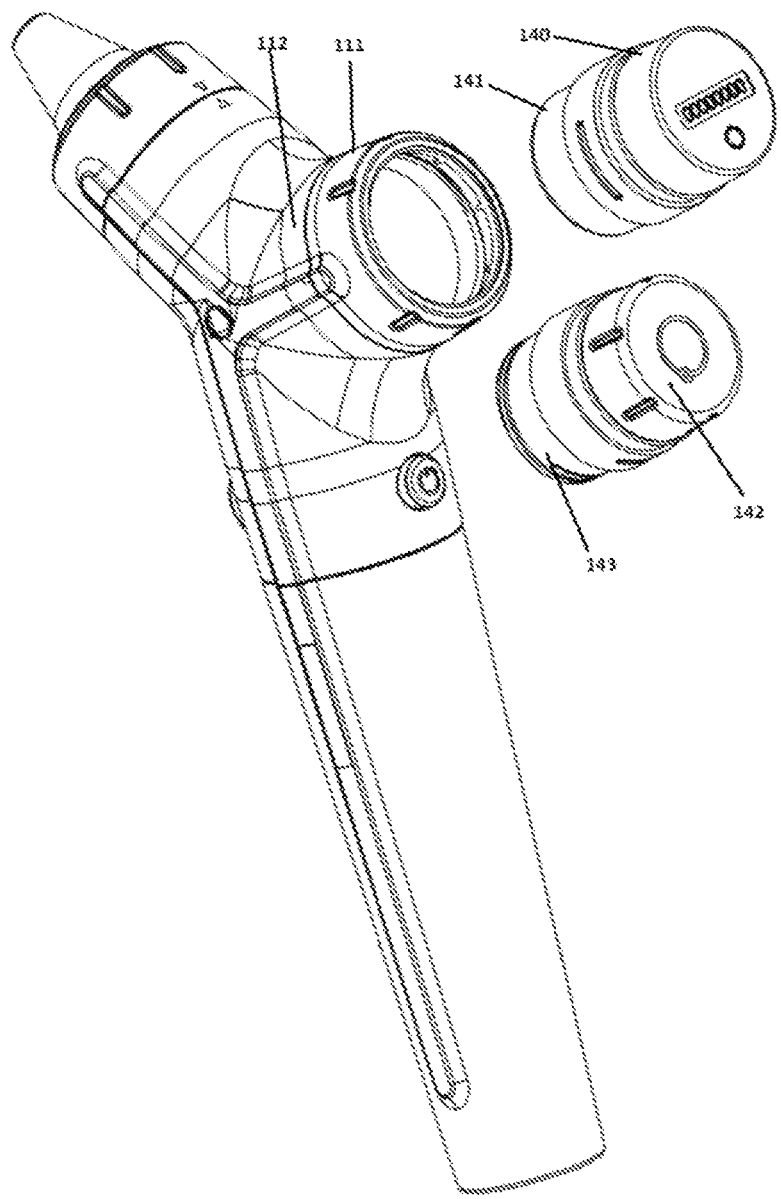
FIG. 25 shows an exploded view of the apparatus with the treatment receptacle portion detached.
Figure 26:
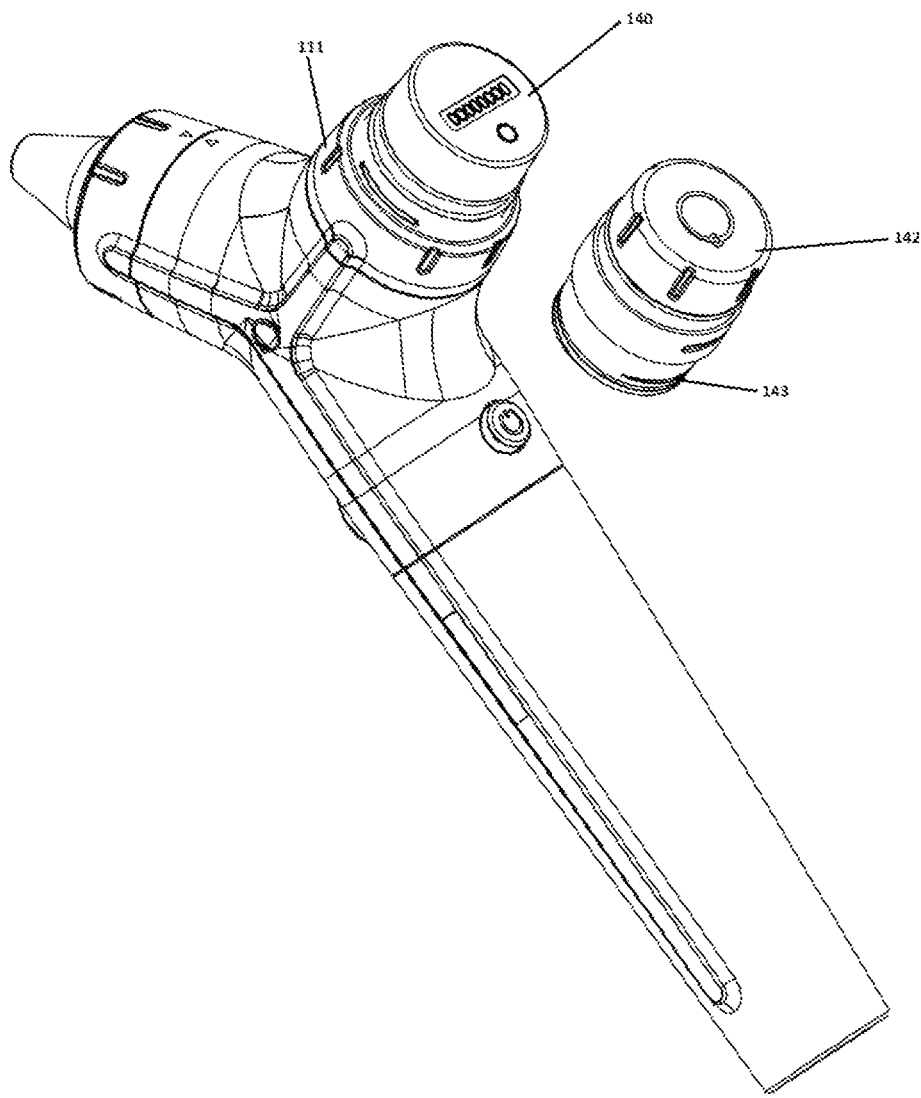
FIG. 26 shows illustrates how the treatment receptacle portion is interchangeable.

FIG. 25 illustrates an exploded view of handheld apparatus 100 with treatment receptacle portion 104 detached. In some embodiments, treatment receptacle portion 104 is interchangeable. In some embodiments treatment receptacle 104 is a gas meter 140 In other embodiments treatment receptacle 104 is a liquid reservoir 142. Gas meter 140 allows the users to control the dosage, pressure, velocity/speed, temperature, and humidity of medical gas by allowing the user to monitor necessary data. Liquid reservoir 142 allows the user to deliver vapor therapies and add liquid soluble additives to therapies. As discussed above, neck 141 of gas meter 140 connects to valve fastener 112 creating an airtight seal. Collar 111 then secures meter 140 to valve housing 103, as illustrated in FIG. 26. Similarly, liquid reservoir 142 attaches to valve fastener 112 through neck 143 and is secured by collar 111.

Figure 27:
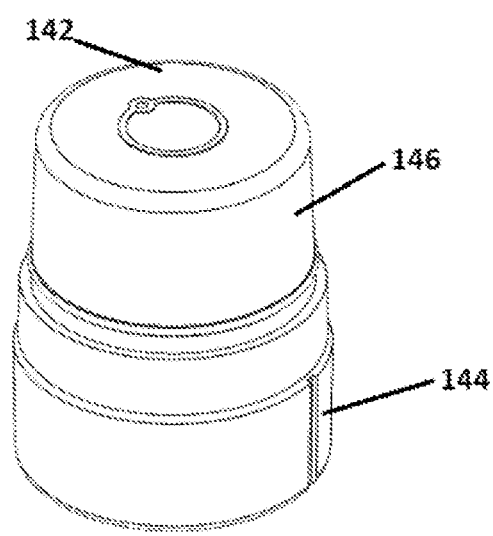
FIG. 27 is an exterior view of the liquid reservoir with the attaching collar removed.
Figure 28:
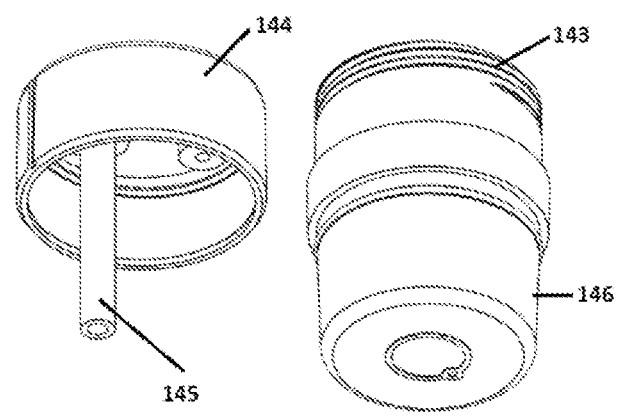
FIG. 28 is an exterior view of the top and bottom portions of the detachable liquid reservoir when not connected to each other.
Figure 29:
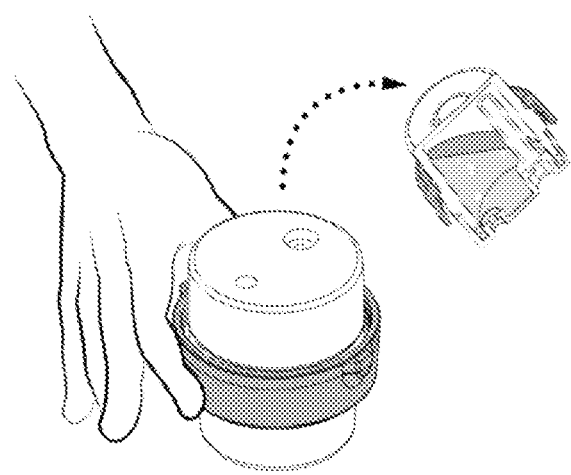
FIG. 29 illustrates how the liquid reservoir may be filled with a liquid from the bottom, transported by holding the attaching collar, and then secured to the valve housing portion of the apparatus by the attaching collar.

FIG. 27 shows the liquid reservoir 142 with a top portion 146 and bottom portion 144. Top portion 146 is separable from bottom portion 144 as seen in FIG. 28. This allows liquid reservoir 142 to be cleaned and filled with a liquid. Top portion 146 connects to bottom portion 144 through collar 143. Top portion 146 and bottom portion 144 may be combined through a threaded connection. In other embodiments top portion 146 and bottom portion 144 are connected through a pressure fit connection. As illustrated in FIG. 28, bottom portion 146 has tube 145 that extends down into the liquid. Tube 145 forces the gas to flow through the liquid and thus collect vapor as it travels through the liquid reservoir. FIG. 29 shows liquid reservoir 142 filled with liquid while detached from apparatus 100.

Figure 30A:
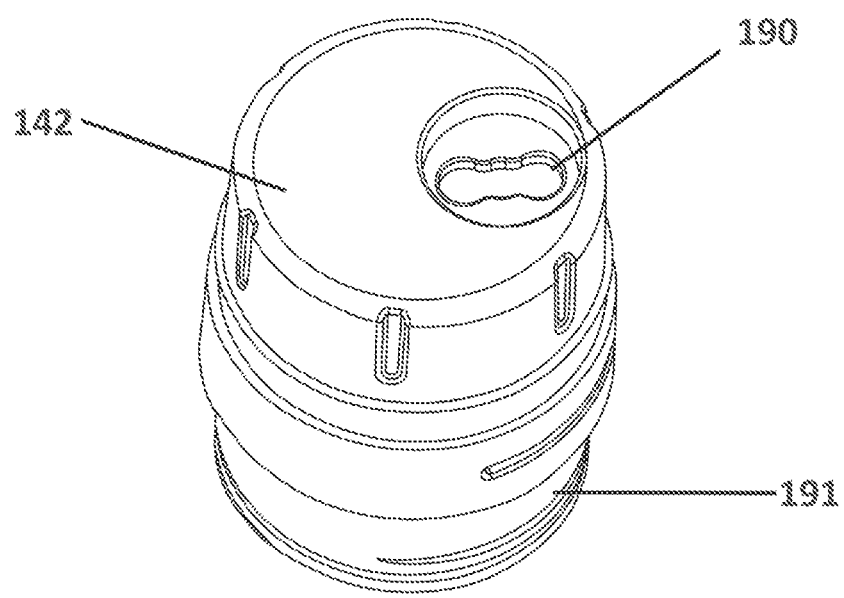
FIG. 30A illustrates an alternative liquid reservoir treatment receptacle where the reservoir is filled without being detached from the apparatus.
Figure 30B:
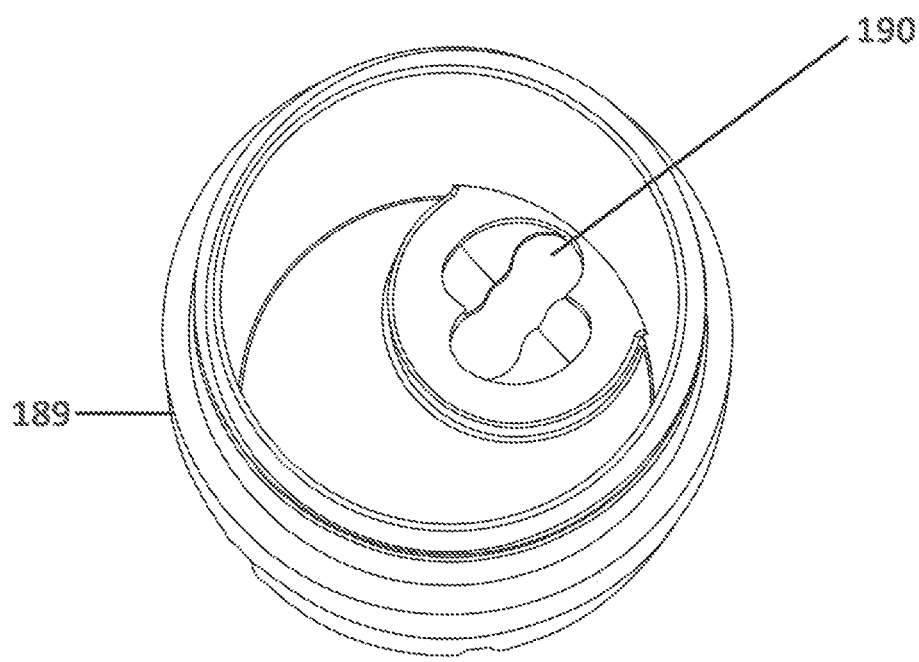
FIG. 30B illustrates an interior view of the top fill liquid reservoir.
Figure 30C:
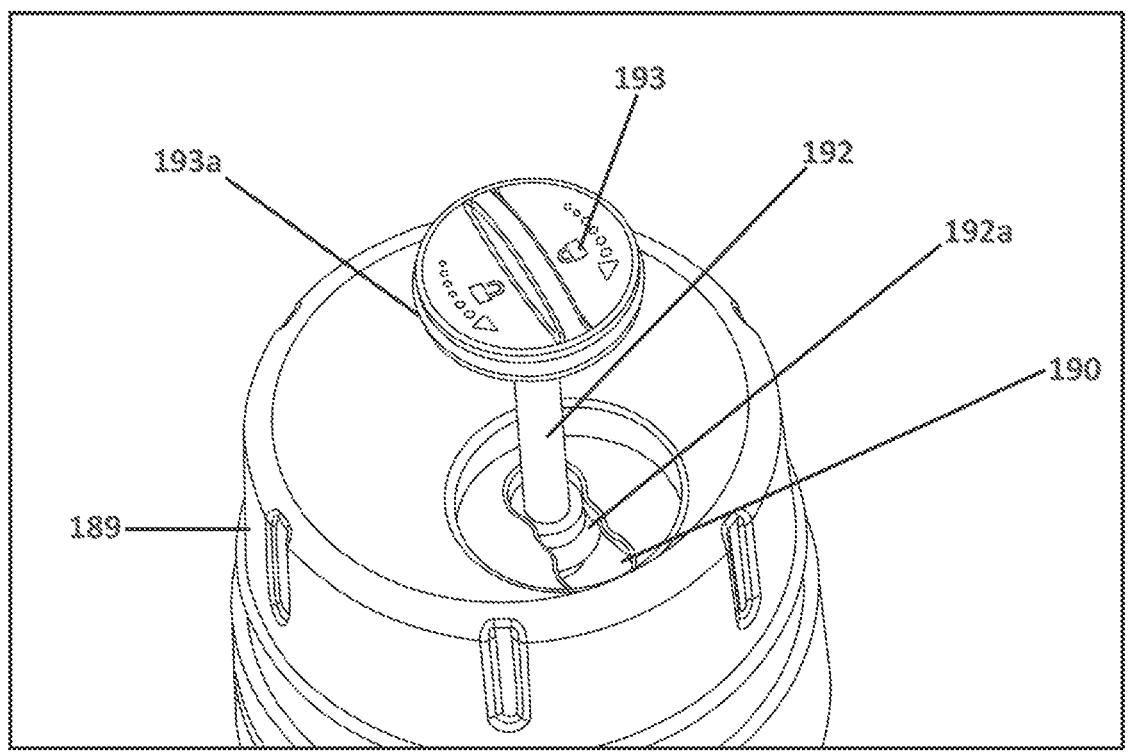
FIG. 30C illustrates how the filling arm of the top fill liquid reservoir fits within the liquid reservoir.
Figure 30D:
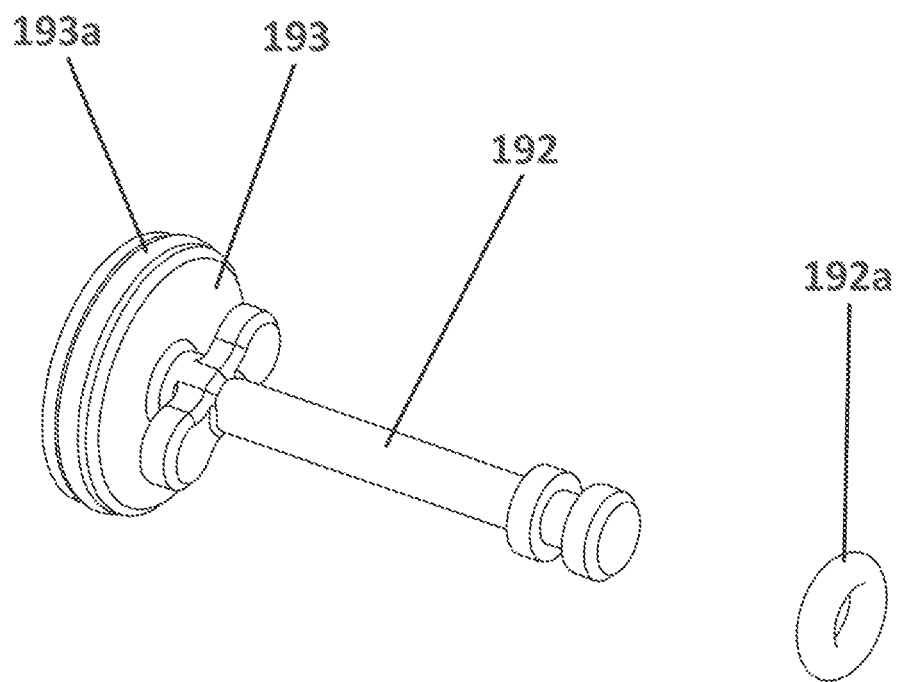
FIG. 30D is an exploded view of the filling arm.
Figure 30E:
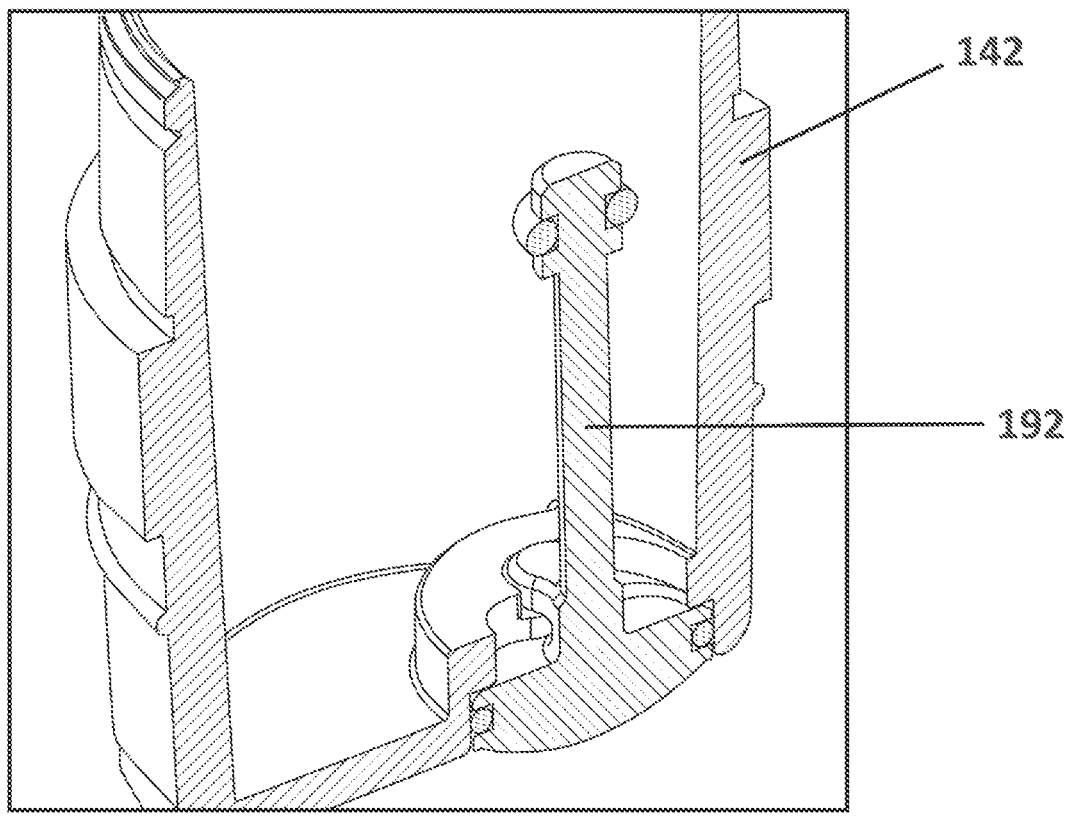
FIG. 30E is an interior view of the filling arm when engaged with the top fill liquid reservoir.

In other embodiments liquid reservoir 142 may be filled with liquid without being removed from apparatus 100. As shown in FIG. 30A, liquid reservoir 142 may be adapted to receive liquid through filling hole 190. In this embodiment liquid reservoir 189 is attached to valve housing 102 through neck 191. FIG. 30B illustrates the interior of top filling liquid reservoir 189. Hole 190 is sealed with cap 193 as shown in FIG. 30C. Sealing arm 192 ensures that cap 193 is not easily removed during operation of apparatus 100. Cap 193 seals liquid reservoir 189 by rotating into a locked position, as seen in FIG. 30C. In some embodiments, sealing arm 192 and cap 193 may be adapted with flexible gaskets 192a and 193a respectively, as seen in FIG. 30D. Gasket 193a prevents sealing arm 192 from being removed from filling hole 190. When top-filled liquid reservoir 189 is sealed with cap 193, sealing arm 192 extends within the reservoir as seen in FIG. 30E.

Figure 31:
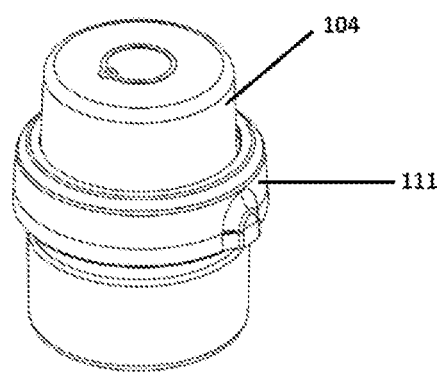
FIG. 31 is an exterior view of an exemplary treatment receptacle with the attaching collar.
Figure 32:
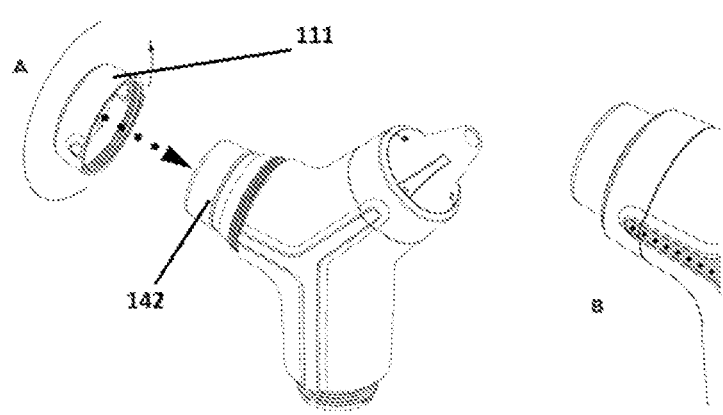
FIG. 32 illustrates the method by which the attaching collar secures the treatment receptacle to the valve housing portion of the apparatus.

FIGS. 31 and 32 show how collar 111 is used to secure treatment receptacle 104 to valve housing portion 103 of apparatus 100. If collar 111 is not fully engaged with valve housing 103, treatment receptacle 104 will not exert a force to push valve pins 120a within the valve 120 into place, and the flow of gas through the system will be obstructed.

Figure 33:
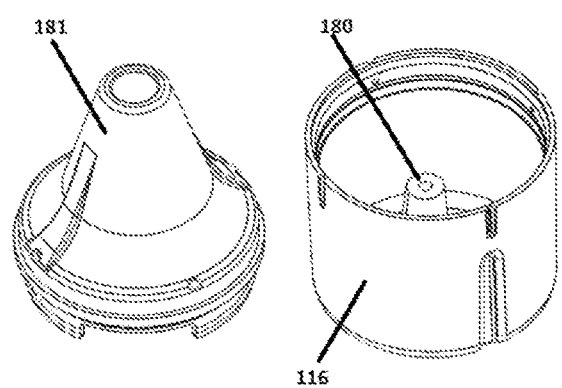
FIG. 33 shows the nozzle cap and the vapor separator of the nozzle portion.
Figure 34:
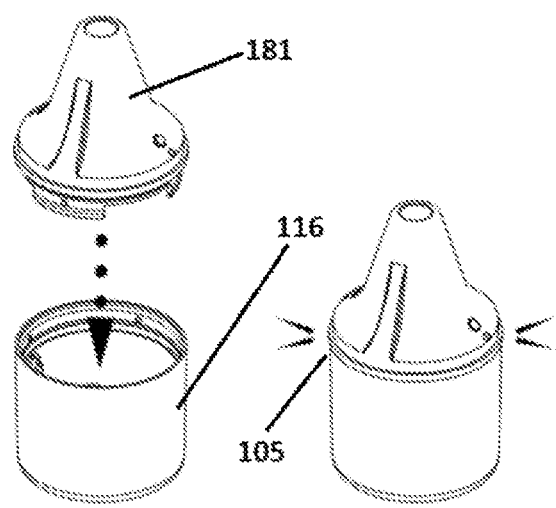
FIG. 34 illustrates how the nozzle cap connects to the gas-vapor separator to form the nozzle portion of the apparatus.
Figure 35:
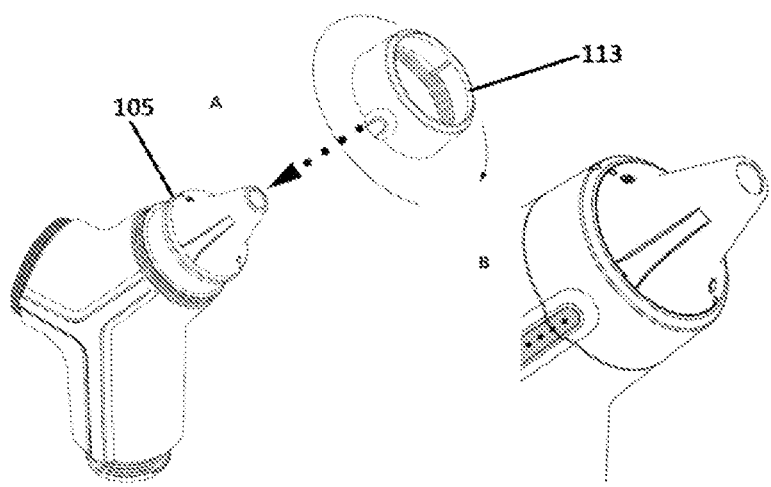
FIG. 35 shows how a collar attaches the nozzle portion of the apparatus to the valve housing unit.
Figure 36:
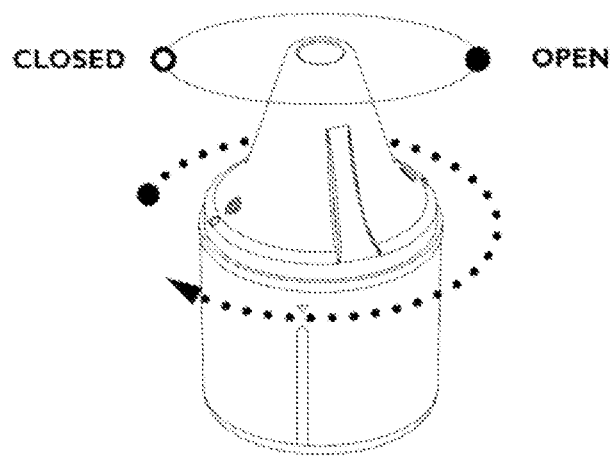
FIG. 36 shows how the nozzle portion may be rotated to adjust an output level of gas-vapor mixture.
Figure 37:
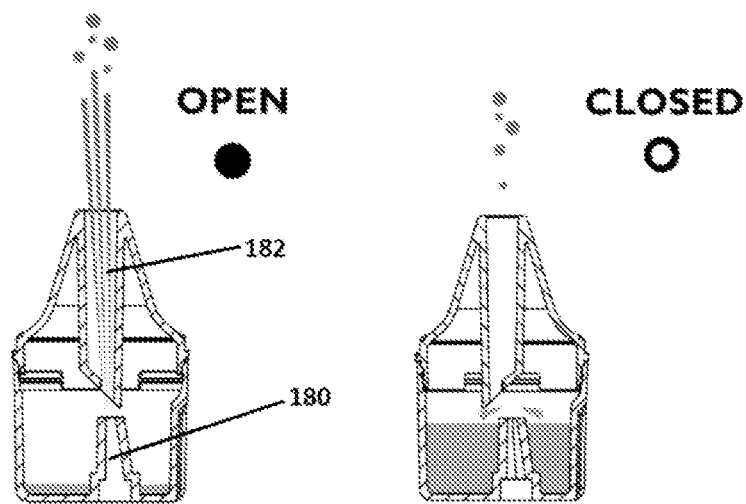
FIG. 37 shows a cross sectional view of how the nozzle portion may be rotated to adjust the level of gas/steam mixture that is blocked from leaving the apparatus and instead is collected in the gas-vapor separator.
Figure 38:
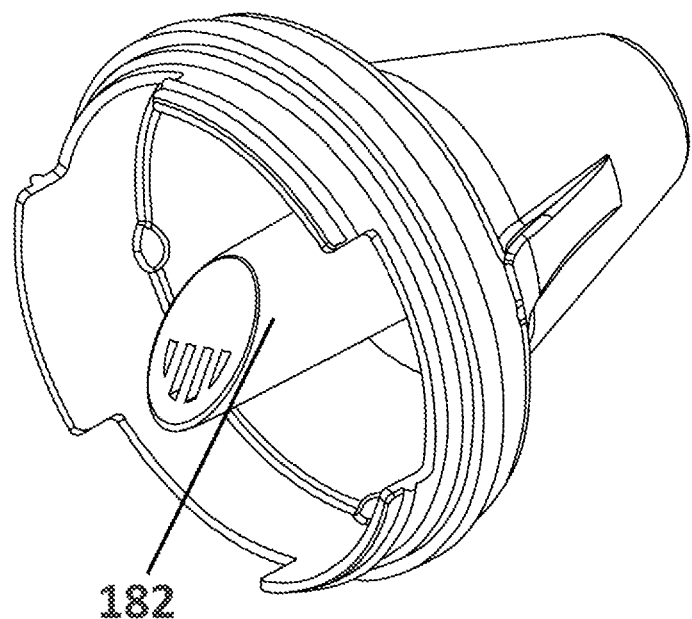
FIG. 38 shows the bottom view of the nozzle cap of the apparatus, when unaffixed to the gas-vapor separator.
Figure 39:
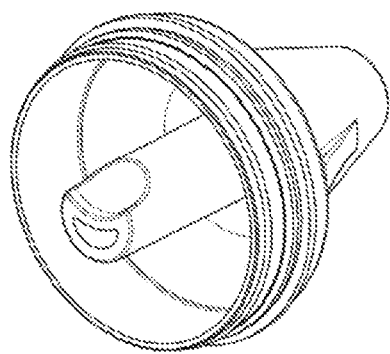
FIG. 39 shows an alternative nozzle design that may accomplish the same gas-vapor restrictive purposes as the FIG. 38 nozzle.

The nozzle portion 105 of apparatus 100 may be further divided into nozzle cap 181, and gas-vapor separator 116 as shown by FIGS. 33 and 34. As discussed above, nozzle portion 105 is affixed to the valve housing system 103 by attaching collar 113, shown in FIG. 35. Nozzle cap 181 may be rotated to control the output of vapor allowed to enter the designated treatment area, shown in FIGS. 36 and 37. Nozzle cap 181 may undergo one hundred and eighty degrees of rotation, where one direction allows vapor to exit through nozzle portion 105 along with the gas, and the other direction prevents steam from exiting through nozzle portion 105. The method by which nozzle portion 105 controls the output of vapor is illustrated by FIG. 37. When nozzle portion 105 is in the open position, output pathway 182 is directly aligned with the input pathway 180 of the gas-vapor separator thus allowing the gas-vapor mixture to exit nozzle 105. When nozzle portion 105 is in the closed position, output pathway 182 of the nozzle is offset from input pathway 180 of the gas-vapor separator, thus the gas-vapor mixture is effectively blocked from exiting nozzle portion 105. FIGS. 38 and 39 further illustrate the structure of output pathway 182 that allow this interaction to occur.

Treatment Processes

Generally, apparatus 100 may be adapted to deliver medical gases to a patient. In some embodiments apparatus 100 is adapted to deliver a mixture of medical gas and water vapor to the patient. In other embodiments apparatus 100 is adapted such that only the medical gas is delivered to the skin, open wound, or various body cavities. In some embodiments apparatus 100 is adapted for delivery of $CO_2$ with water vapor. In some embodiments the $CO_2$/water vapor treatments are applied where skin barriers need to be broken non-invasively and pain free. In other embodiments the $CO_2$/water vapor treatments are applied where skin barriers do not need to be broken such as gas application to open wounds and various body cavities.

Transdermal Delivery of Medical Gases

Scientists and researchers have explored ways of delivering drugs, such as medical gases, to the patient through the skin, which can be a safer, non-invasive method of delivery. Transdermal drug delivery offers numerous advantages over more traditional drug delivery forms. Transdermal delivery methods can avoid problems caused by oral dosages, such as gastrointestinal irritations, drug metabolism issues and interference due to the presence of food, and it may be administered to nauseated or unconscious patients. Transdermal methods are non-invasive compared to intravenous means and, due to the steady diffusion of the drug through the skin, they offer more consistent drug infusions, even in localized areas over several days, thereby reducing "peaks" that may cause side effect. Transdermal delivery is simpler and painless for patients and thus, more likely to achieve patient adherence to therapy regimens.

However, a disadvantage of such drug delivery is that skin typically has a natural "barrier function" to prevent foreign substances from entering the body. Indeed, skin evolved for the purpose of protecting against unwanted substances such as toxins and microorganisms. Thus, drug absorption through the skin is difficult, and an effective transdermal delivery system must find ways to efficiently pass through this barrier.

A mentioned above, in some embodiments apparatus 100 is adapted for the delivery of $CO_2$ gas to a patient. $CO_2$ gases are especially suited to such transdermal drug deliveries without side effects such as localized irritations. This is because $CO_2$ has 25 times greater permeability to cell membranes than $O_2$. Further $CO_2$ is 30 times more soluble in water than $O_2$. $CO_2$ also easily dissolves into oil. Skin has a structure similar to that of water and oil, which may explain why skin can also easily absorb $CO_2$.

$CO_2$ increases tissue $O_2$, due to the $O_2$ conveyance protein called hemoglobin contained in red blood cells, as well as the Bohr effect. The supply of $O_2$ for supporting the activities of a creature is mainly performed by hemoglobin in red blood cells. After $O_2$ binds to the hemoglobin in the lungs, it is released in the tissues. In the presence of increased $CO_2$ in the blood within the tissues, the pH in the tissues decreases due to the conversion of the $CO_2$ to bicarbonate molecules and acidic protons. With decreased pH, the $O_2$ more easily dissociates from the hemoglobin. This reduction in $O_2$ affinity to hemoglobin is referred to as the "Bohr effect". Due to this effect, the increased $O_2$ dumping in the tissues results in the many positive medical effects described above.

Various research studies conducted have confirmed that $CO_2$ absorbed in this manner has positive effects such as blood vessel dilations leading to healthier skin, greater $O_2$ supply to the cells resulting the activation of cell metabolisms and improvements in skin texture, and anti-aging, and wound healing effects. Such systems for artificially and enhancing the positive effects of $CO_2$ balneotherapy have a long history as a well-known therapy in Europe, Japan and many other countries. These therapies have had at least 120 years of success at healthcare establishments for treating major conditions such as cardiovascular conditions (high blood pressure and atherosclerosis), diabetes mellitus, arthritis, and osteoporosis without side effects. Furthermore, studies have shown that the addition of mineral salts and/or essential oils, or other additional substances, to the water may further enhance the positive effects of $CO_2$ balneotherapy.

In addition to the treatment of major conditions that affect millions of people around the globe, the above-described $CO_2$ gas therapies have many other positive effects on the human organism, including exercising and refreshing the body, strengthening internal organ functions, relaxation and stress reduction benefits, anti-bacterial and blood cleansing tendencies, muscle and nervous system stimulations, skin beautification effects, etc. Evidence also shows that carbon dioxide has bactericidal effects in the supercritical (liquid) state that can only be obtained at very high pressure.

Although transdermally absorbed $CO_2$ may be referred to as "carbon dioxide gas", in fact, the absorbed $CO_2$ is actually not in the form of visible bubbles. Instead, transdermally absorbed carbon dioxide exists in the form of invisible water-dissolved molecular $CO_2$. The positive medical effects described are obtained through exposure to this $CO_2$/water vapor mixture. For example, if one simply blows $CO_2$ bubbles from a tube onto the skin, no cosmetic effects can be obtained because the $CO_2$ is hardly absorbed into the skin in the form of bubbles.

The embodiments of the present disclosure provide a highly simple means for the topical application and transdermal delivery of $CO_2$ or other such medical gases or biologically beneficial oils, minerals, and other pharmaceuticals in gaseous state utilizing a apparatus that is very simple and cost effective to manufacture and to use. The embodiments of the present disclosure are mechanical and require no electricity or technical assistance to operate, leave no residual, and are easy to clean and maintain. The apparatus is conveniently small in size and mobile and easy to use as one would screw in a cartridge into a soda syphon, or screwing in a light bulb. The apparatuses of the present disclosure are equally applicable for both commercial and home usage, and makes medical treatments as easy, pleasant and relaxing as taking a warm bath.

Figure 40:
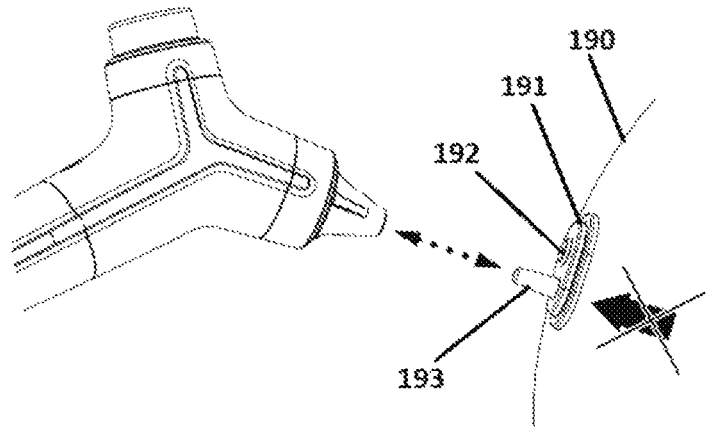
FIG. 40 illustrates the method by which the apparatus introduces gases into the covering.
Figure 41:
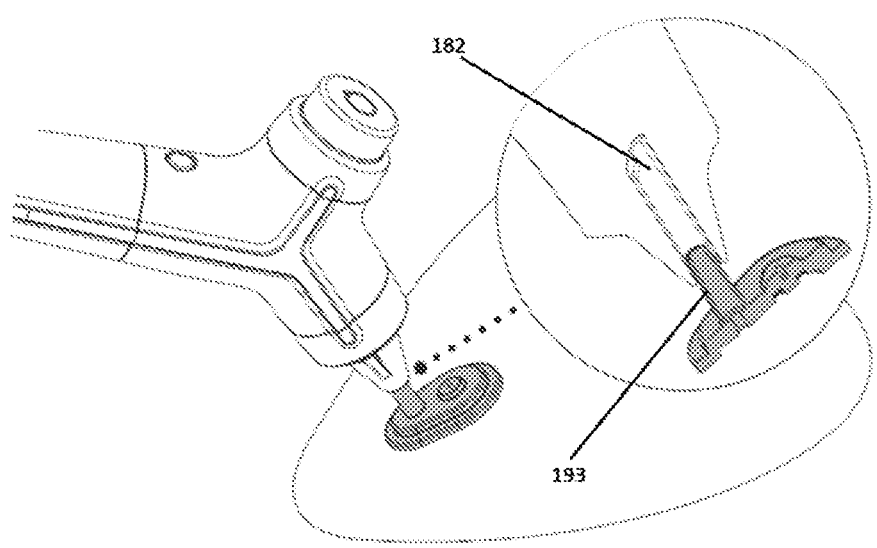
FIG. 41 illustrates a pressure release valve useable with the apparatus that prevents over-inflation of the cover.
Figure 42:
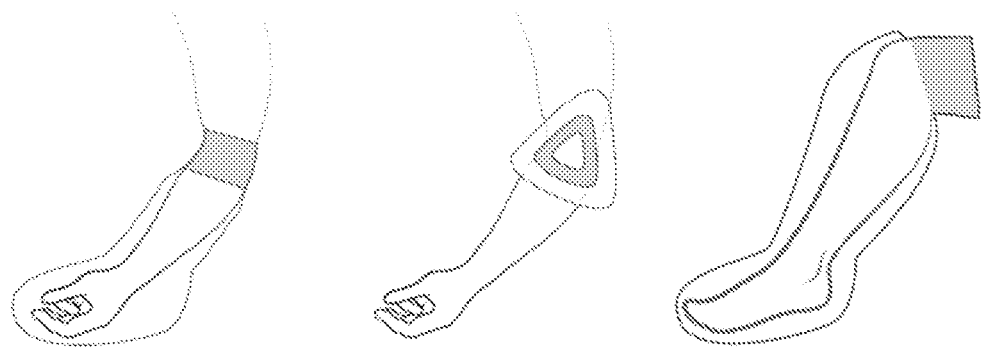
FIG. 42 provides exemplary coverings.

FIG. 40 shows how the nozzle portion 105 of apparatus 100 attaches to body covering 190 of the designated treatment area. Body covering 190 has a pressure sensitive valve 191, adapted with check valve 192 and flexible tubing 193. Flexible tubing 193 fits within 182 of nozzle portion 105 allowing for the delivery of medical gases to the body covering 190 (FIG. 42). Pressure sensitive valve 191 has a pressure release function 192 that automatically opens and releases gas when the interior pressure reaches a 0.33 PSI or more. FIG. 42 provides an illustration of different body coverings 190. It is envisioned that body covering 190 can be adapted for any part of the body.

In addition to the above treatment methods, it is also encompassed within the present invention that the apparatus may be used to deliver the gas-vapor mixture to the skin without the use of an absorption suit. Transdermal delivery of the $CO_2$ may be accomplished by "misting" the skin by holding an open end of the delivery tube (with the other end leading to the delivery unit) close to the skin (approximately 1 or 2 inches away, for example) or by "spraying" the skin with the high concentration of $CO_2$. The absorption suits may produce higher efficacies because they keep the fog-like mist enclosed around body parts for controllable periods. However, due to the above-described high skin permeability of $CO_2$, effective treatments may still occur without such suits.

Intra-Cavity Delivery of Medical Gases

As discussed above, studies clearly demonstrate that $CO_2$ gas has significant physiological responses that can be generally applied to various diseases. Several studies show that elevated $CO_2$ concentrations will moderate the inflammatory process. Exemplary disease that could benefit from $CO_2$ therapy include. cystitis, endometritis, vaginitis, otitis, and colitis. Previously this could only be accomplished by using systemic medications such as non-steroidal anti-inflammatory medications with their well described side effects. $CO_2$ is a clearly a novel approach to this difficult problem.

The treatment of inflammation with $CO_2$ may be effectuated by applying $CO_2$ to organs or cavities in the body thus providing a local treatment of inflammatory diseases. Exemplary organs and cavities include but are not limited to the bladder, uterus, vagina, oral cavity, nasal sinuses, ear canal, and rectum.

Figure 44:
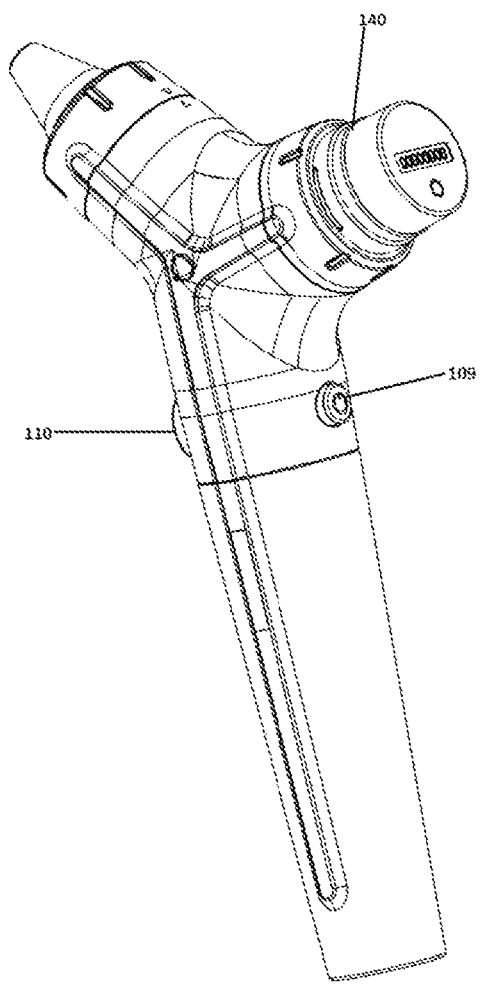
FIG. 44 illustrates the apparatus where the treatment receptacle portion is a meter for determining the amount of therapeutic gas being delivered through the nozzle.
Figure 45:
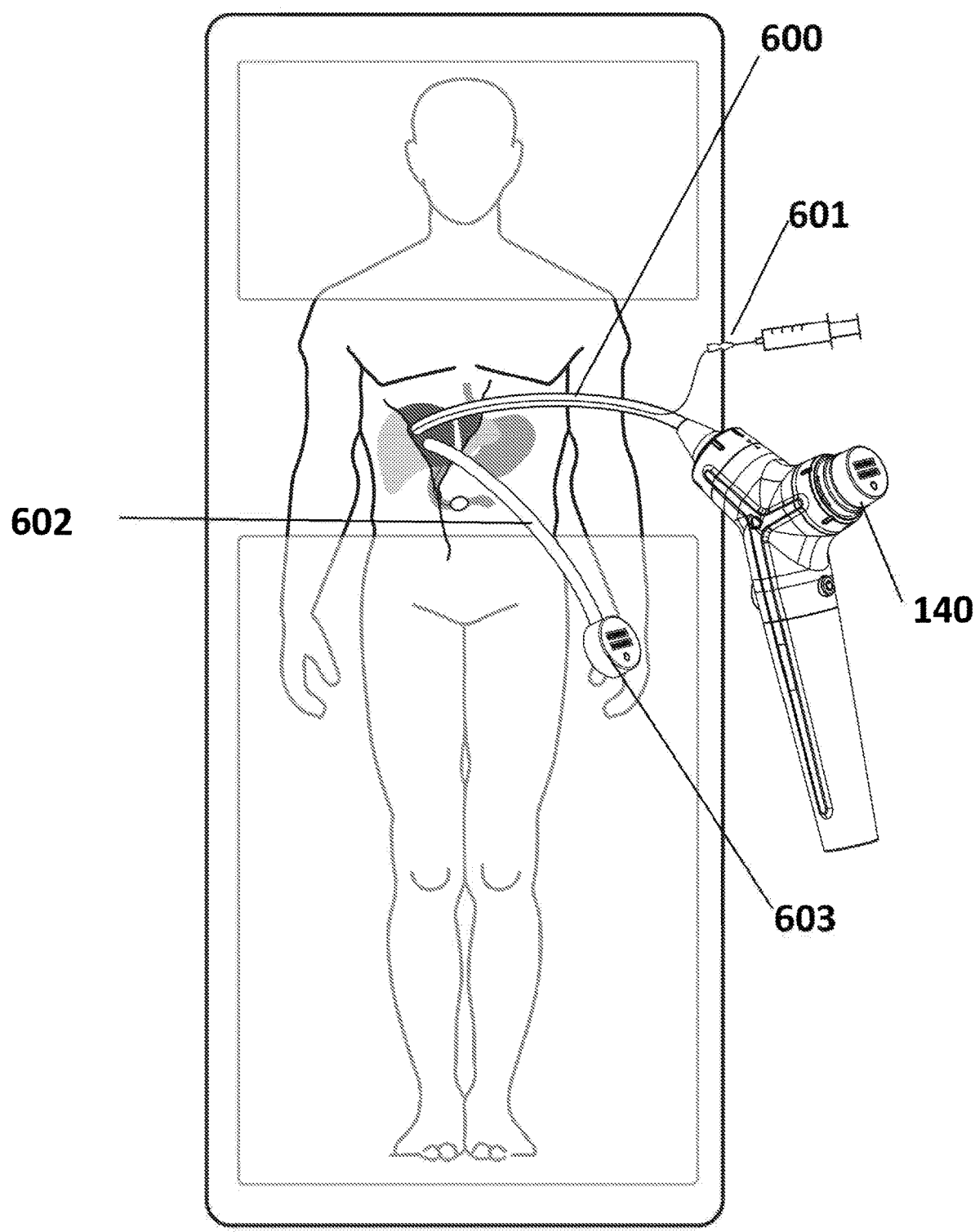
FIG. 45 illustrates the use of the apparatus for intra-cavity delivery of a therapeutic gas to the liver.

Apparatus 100 may be adapted for used in intra-cavity treatments $CO_2$. As shown in FIG. 44, apparatus 100 is outfitted with treatment receptacle gas meter 140. The flow of gas through apparatus 100 is control by flow-control dial 110. Medical gas is delivered to the patient by outfitting nozzle 105 with tubing 600. Tubing 600 is then coupled with the body cavity as shown in FIG. 45. Apparatus 100 is then engaged to deliver the medical gas. The cavity is first flushed with the gas, with the excess gas being removed by tubing 603. Tubing 603 may be outfitted with meter 602 to allow the user to determine the flow gas exiting the cavity. Tubing 600 further comprises port 601 which allows the user to sample the concentration of gas delivered by apparatus 100.

Figure 46:
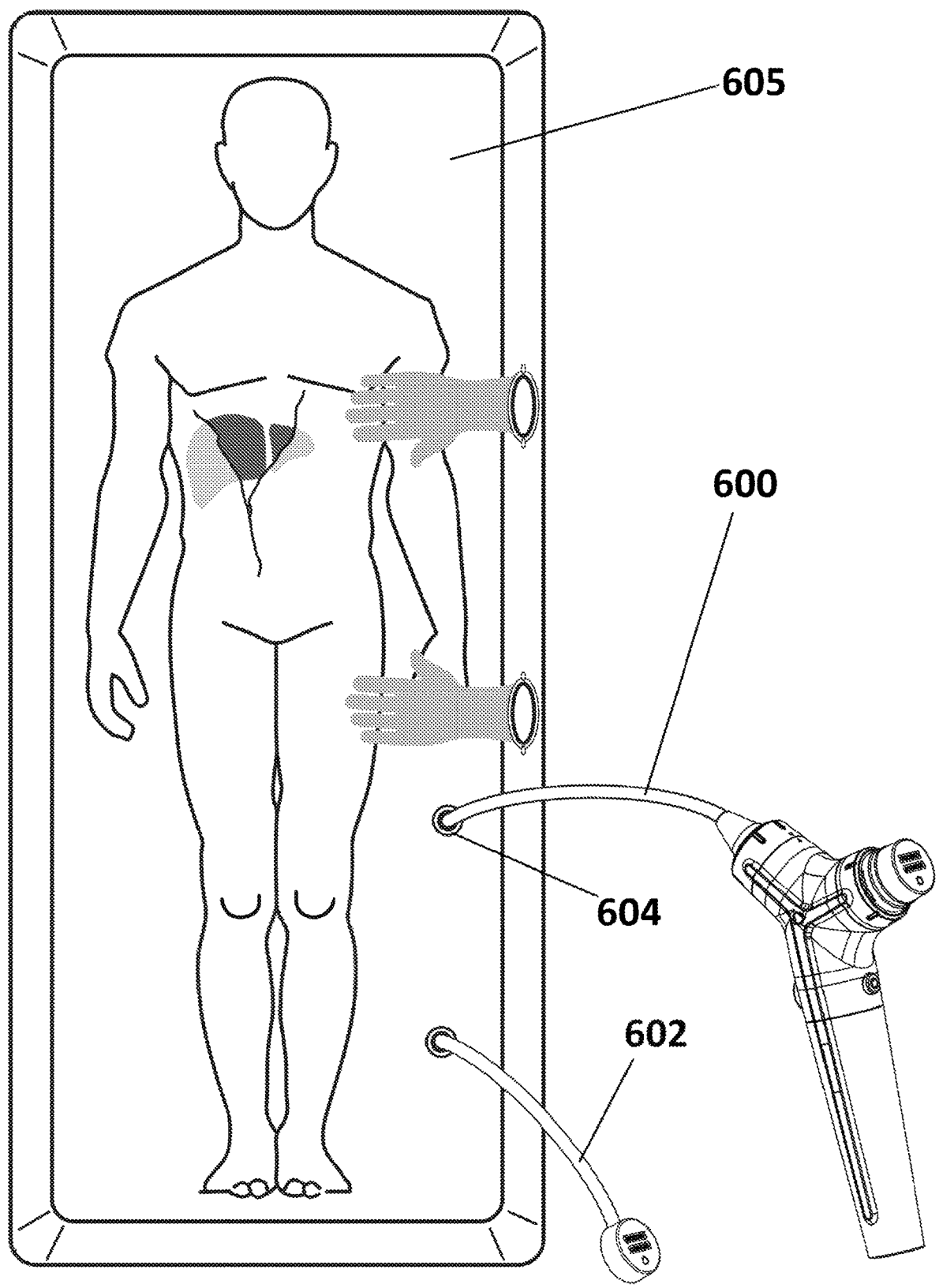
FIG. 46 illustrates the use of the apparatus for intra-cavity delivery of a therapeutic gas utilizing an gas treatment chamber

In addition to direct delivery to a cavity, the patient may be place inside incubator chamber 605 for open body treatment during surgery or other medical procedures as shown in FIG. 46. In this embodiment tubing 600 is inserted into inlet port 604 of chamber 605. Chamber 605 is then flushed with the medical gas. The outflowing gas exiting through tubing 603 inserted in port 608. The outflowing gas is monitored by meter 603.

Figure 47:
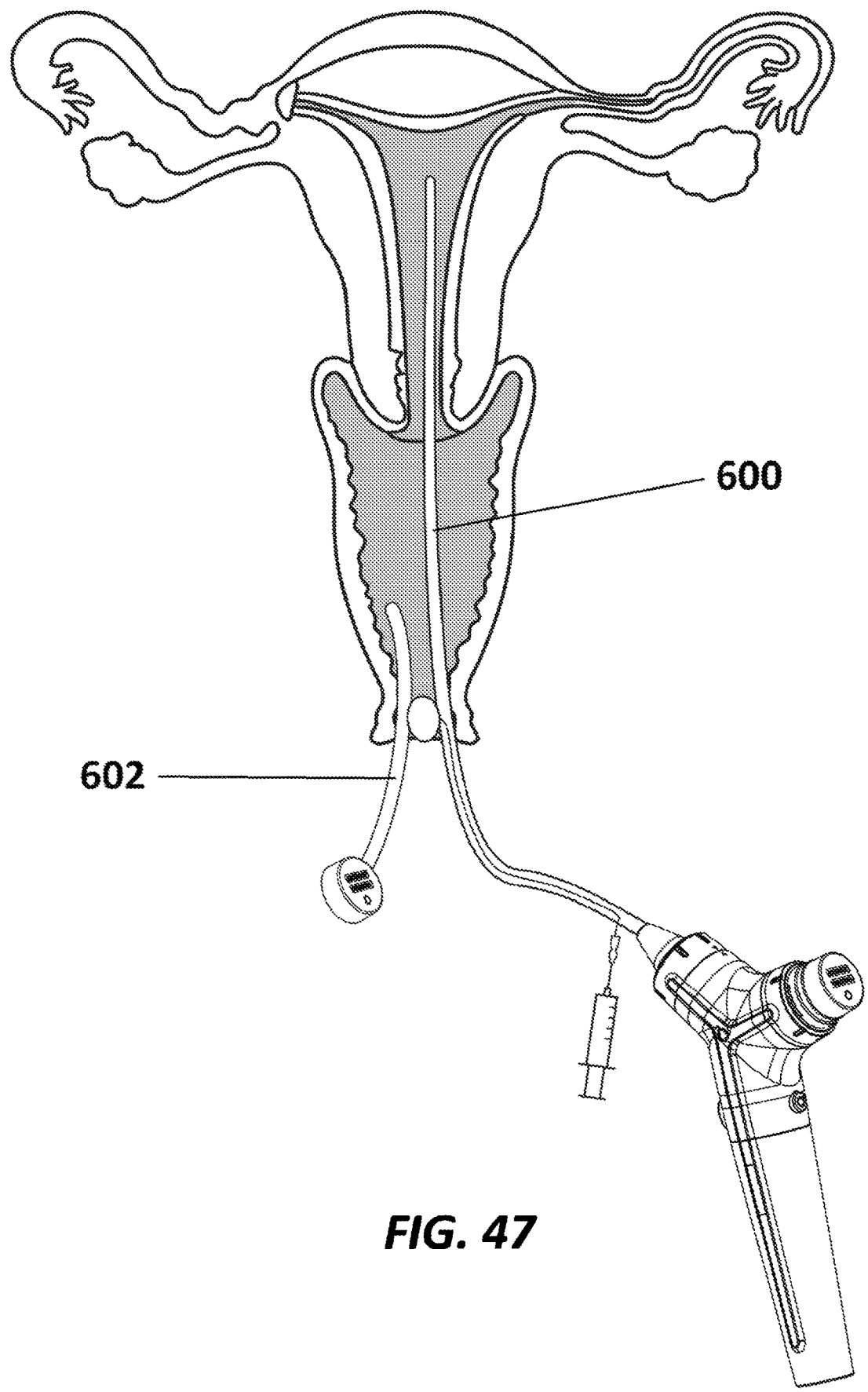
FIG. 47 illustrates the use of the apparatus for delivery of therapeutic gas to the uterus and ovaries as a treatment for endometriosis.

In other embodiments apparatus 100 may be used to deliver medical gases directly to organs. As illustrated in FIG. 47, nozzle 105 is outfitted with tubing 600 which is then inserted into the organ cavity. The organ is then flushed with the medical by allowing the gas to flow through tubing 600 and out tubing 602. Tubing 602 may be outfitted with meter 603 to allow the user to determine the flow gas exiting the cavity. Tubing 600 further comprises port 601 which allows the user to sample the concentration of gas delivered by apparatus 100. In some embodiments port 601 may be used to add additional pharmaceutical therapies to the intra-cavity space. Apparatus 100 may be adapted to deliver gas to the uterus, ovaries, lungs, and other cavities of the body.

Further details regarding testing of $CO_2$ delivery, and in particular using a similar apparatus, are described in U.S. Pat. No. 9,713,570, commonly assigned with the present application, the disclosure of which is hereby incorporated by reference in its entirety.

The foregoing description of the embodiments of this invention has been presented for purposes of illustration and description. It is not intended to be exhaustive or to limit the embodiments of the invention to the form disclosed, and, obviously, many modifications and variations are possible. For example, although in the present disclosure a certain size and arrangement of components of an apparatus for transdermal delivery of $CO_2$ is described, it is noted that the present invention is not limited thereto. Various other sizes of apparatuses or arrangements are possible as well.

Furthermore, the scope of the present disclosure can also encompass the use of a wide variety of medical, pharmaceutical or purified gases and related substances. In general, such gases present excellent opportunities for medical innovations, because gases are important biological messenger molecules and show promising biological effects, naturally occurring gases appear to have low toxicity profiles, their properties may enable the application of other medical principles. Current uses of gases in medicine have been minimally explored. Thus, the present invention can provide an effective medical apparatus or drug delivery apparatus for the safe, non-invasive injection of medical gases into the human or animal organism through the pores of the skin.

The present invention may even have diversified application possibilities, including those in preventive medicine, sports medicine, veterinary medicine, the space biomedical industry (e.g., muscle and bone less in space), rehabilitation medicine, and troop health support for the military. One may also foresee additional applications of the dispersion technologies of the present invention in fields such as waste water treatment and gas-liquid dispersions (i.e., as a soft drink production alternative). Such modifications and variations that may be apparent to a person skilled in the art are intended to be included within the scope of this invention as defined by the accompanying claims.

The invention claimed is:

1. A handheld therapeutic apparatus for the delivery of therapeutic gases, the apparatus comprising:
    a handle portion adapted to receive a gas cartridge within an interior of the handle portion;
    a valve housing portion adapted to house a valve system comprising a three-way valve, the valve housing portion being detachably joinable to the handle portion at a collar and including a gas cartridge piercing pin that engages the gas cartridge when the handle portion is joined to the valve housing portion;
    a treatment receptacle portion detachably joinable to the valve housing portion at an attaching collar, the treatment receptacle portion being in fluid communication with the valve system and adapted to receive a treatment module; and
    a nozzle portion in fluid communication with the valve system.

2. The handheld therapeutic apparatus of claim 1, wherein the valve system contains one
    or more flow control pins.

3. The handheld therapeutic apparatus of claim 1, wherein the handle portion
    contains a gas cartridge clip capable of holding the gas cartridge in place.

4. The handheld therapeutic apparatus of claim 3, wherein the handle portion
    includes at least one channel arranged to receive a portion of the gas cartridge clip, and at least one window providing visibility of at least one of the gas cartridge or written indicia on the gas cartridge clip.

5. The handheld therapeutic apparatus of claim 1, wherein the handle portion
    is compatible:
    with at least one of gas cartridges of varying size or with gas delivery via a connection to an external gas source.

6. The handheld therapeutic apparatus of claim 1, wherein the nozzle portion rotates to control the gas-vapor concentration.

7. The handheld therapeutic apparatus of claim 1, wherein the nozzle portion attaches to a body member covering.

8. The handheld therapeutic apparatus of claim 1, wherein the nozzle portion attaches to a gas chamber.

9. The handheld therapeutic apparatus of claim 1, wherein the nozzle portion attaches to tubing.

10. The handheld therapeutic apparatus of claim 1, wherein the apparatus has a gas flow-control dial for regulating the flow of gas.

11. The handheld therapeutic apparatus of claim 1, wherein the apparatus has an actuator button that starts and stops the flow of gas.

12. A gas cartridge assembly for use in the handheld treatment apparatus, comprising:
    a silicone seal including a sealing portion having a plurality of perforations, and
    a gas cartridge,
    wherein the silicone seal is attached to the gas cartridge at a pierceable cartridge aperture of the gas cartridge.

13. The gas cartridge assembly of claim 12, wherein the gas containing cartridge silicone seal creates an airtight seal when pierced by a piercing pin.

14. A handheld therapeutic apparatus for the delivery of therapeutic gases, the apparatus comprising:
    a valve system within a valve housing portion, the valve system comprising a three-way valve with control pins for controlling the flow of gas through the valve system;
    a handle portion adapted to receive a gas source, the handle portion being removably attachable to the valve housing portion;
    a treatment receptacle portion removably attachable to the valve housing portion;
    a nozzle portion removably attachable to the valve housing portion; and
    wherein the valve housing portion is adapted to engage the treatment receptacle portion and the nozzle portion such that the receptacle treatment portion and nozzle portion are in fluid communication with the valve system.

15. A handheld therapeutic apparatus for the delivery of therapeutic gases, the apparatus comprising:
    a valve system comprising a three-way valve with control pins for controlling the flow of gas through the valve system;
    a handle portion adapted to receive a gas source;
    a treatment receptacle portion;
    a nozzle portion; and
    a valve housing portion adapted to house the valve system and adapted to engage the treatment receptacle portion and the nozzle portion such that the receptacle treatment portion and nozzle portion are in fluid communication with the valve system;
    wherein the treatment receptacle portion is a gas meter.

16. The handheld therapeutic apparatus of claim 14 wherein the treatment receptacle is a liquid reservoir.

17. The handheld therapeutic apparatus of claim 14, wherein the apparatus further comprises a piercing pin and piercing pin housing.

18. A method of treating an area of an individual user with medical or therapeutic gases, the method compromising:
    a) assembling a handheld therapeutic apparatus, said therapeutic apparatus comprising:
        (i) a valve system comprising a three-way valve with control pins for controlling the flow of gas through the valve system;
        (ii) a handle portion adapted to a gas cartridge assembly;
        (iii) a treatment receptacle portion;

(iv) a nozzle portion; and
(v) a valve housing portion adapted to house the valve system and adapted to engage the treatment receptacle portion and the nozzle portion such that the receptacle treatment portion and nozzle portion are in fluid communication with the valve system;

b) placing the gas cartridge assembly in the handle portion;

c) attaching the handle portion to the valve housing such that a piercing pin pierces the gas cartridge allowing gas to flow from the gas cartridge through the valve system to the treatment receptacle portion and the nozzle portion;

d) delivering the gas to the patient through the nozzle portion.

* * * * *